(12) United States Patent
Neriishi et al.

(10) Patent No.: US 7,220,389 B2
(45) Date of Patent: May 22, 2007

(54) BIOCHEMICAL ANALYSIS UNIT AND METHOD OF PRODUCING THEREOF

(75) Inventors: Keiko Neriishi, Kanagawa (JP); Yuichi Hosoi, Kanagawa (JP); Katsuhiro Kohda, Kanagawa (JP); Masahiro Eto, Tokyo (JP); Akifumi Kato, Kanagawa (JP); Kenji Nakajima, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 555 days.

(21) Appl. No.: 10/147,826

(22) Filed: May 20, 2002

(65) Prior Publication Data

US 2002/0197568 A1  Dec. 26, 2002

(30) Foreign Application Priority Data

| May 21, 2001 | (JP) | ............................. | 2001-150414 |
| Jun. 20, 2001 | (JP) | ............................. | 2001-186287 |
| Jun. 26, 2001 | (JP) | ............................. | 2001-192895 |
| Jun. 26, 2001 | (JP) | ............................. | 2001-192896 |
| Sep. 27, 2001 | (JP) | ............................. | 2001-298368 |

(51) Int. Cl.
  *B01L 11/00* (2006.01)
(52) U.S. Cl. .......................... 422/101; 422/56; 422/99; 435/287.2; 435/287.7; 435/288.4; 436/518; 436/164
(58) Field of Classification Search .................... 435/6, 435/7.1, 283.1, 287.2, 287.7, 287.8, 288.4, 435/288.7; 422/52, 56, 57, 82.05, 99, 101; 436/518, 524, 525, 164
See application file for complete search history.

(56) References Cited

U.S. PATENT DOCUMENTS

| 4,493,815 | A | * | 1/1985 | Fernwood et al. | .......... 422/101 |
| 4,918,133 | A | * | 4/1990 | Moriya et al. | .............. 524/518 |
| 5,087,820 | A | | 2/1992 | Kearns et al. | |
| 5,380,644 | A | | 1/1995 | Yonkoski et al. | |
| 5,545,531 | A | * | 8/1996 | Rava et al. | ..................... 435/6 |
| 5,807,522 | A | | 9/1998 | Brown et al. | |
| 6,171,780 | B1 | * | 1/2001 | Pham et al. | ................... 435/4 |
| 2001/0026917 | A1 | | 10/2001 | Neriishi et al. | |

FOREIGN PATENT DOCUMENTS

| DE | 100 35 704 A1 | 3/2001 |
| EP | 1 037 071 A2 | 9/2000 |

(Continued)

OTHER PUBLICATIONS

Japanese Abstract No. 2000338042, dated Dec. 8, 2000.
Japanese Abstract No. 2001033458, dated Feb. 9, 2001.

Primary Examiner—Long V. Le
Assistant Examiner—Gary W. Counts
(74) Attorney, Agent, or Firm—Sughrue Mion, PLLC

(57) ABSTRACT

The biochemical analysis unit has a base plate and absorptive regions. The absorptive regions are surrounded by the base plate formed of materials which shield a radioactive ray and a light. In the absorptive regions are applied and absorbed specific binding substances to be bound with substances derived from a living organism that are labeled with labeling substances for generating the radioactive ray or the light. The base plate prevents the specific binding substances from penetrating in the other absorptive regions. When an analysis of data of the radioactive ray and the light is carried out, an image of the radioactive ray and the light is generated without noises.

23 Claims, 31 Drawing Sheets

FOREIGN PATENT DOCUMENTS

| | | | |
|---|---|---|---|
| GB | 0776700 | * | 12/1996 |
| JP | 48-40050 | | 6/1973 |
| JP | 55-12145 | | 1/1980 |
| JP | 58-37842 | | 3/1983 |
| JP | 58-69281 | | 4/1983 |
| JP | 59-56479 | | 3/1984 |
| JP | 59-75200 | | 4/1984 |
| JP | 60-90288 | | 5/1985 |
| JP | 60-101179 | | 6/1985 |
| JP | 62-170950 | | 7/1987 |
| JP | 63-188135 | | 8/1988 |
| JP | 64-70882 | | 3/1989 |
| JP | 64-70884 | | 3/1989 |
| JP | 2-276997 | | 11/1990 |
| JP | 4-3962 | | 1/1992 |
| JP | 6-301140 | | 10/1994 |

* cited by examiner

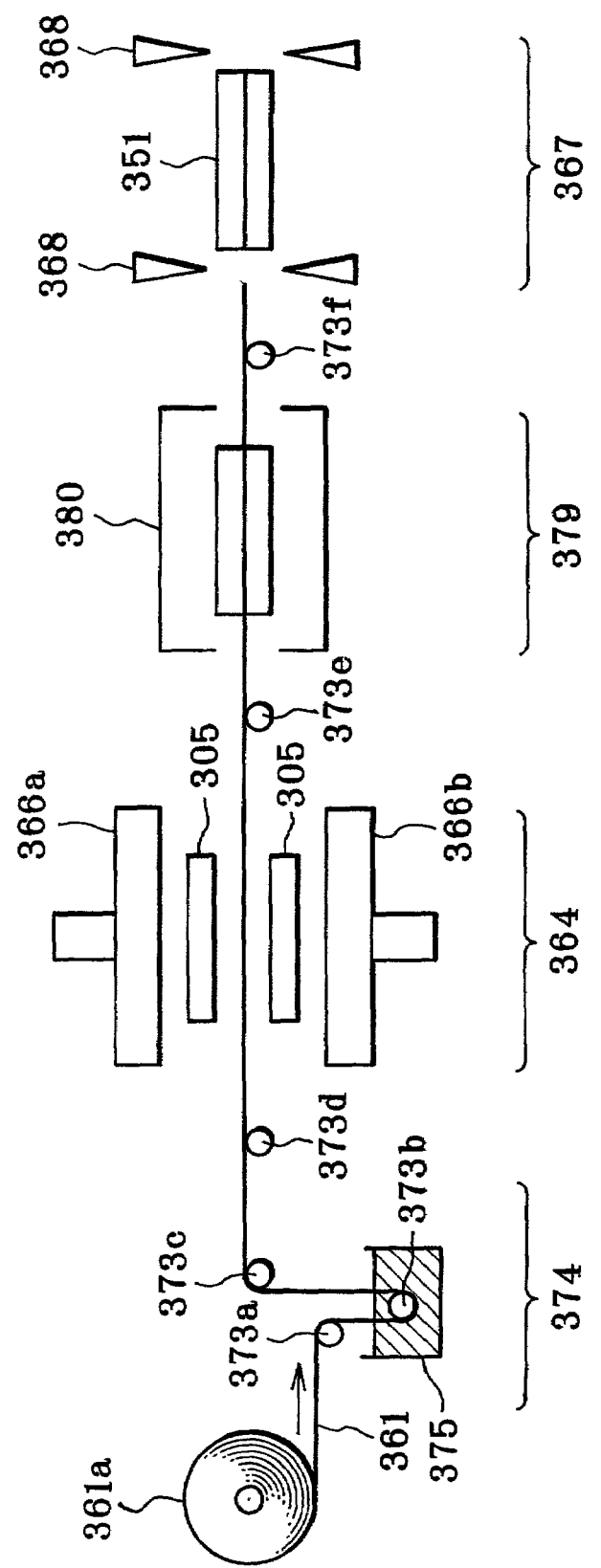

BIOCHEMICAL ANALYSIS UNIT AND METHOD OF PRODUCING THEREOF

BACKGROUND OF THE INVENTION

1. Field of the Invention

The present invention relates to a biochemical analysis unit and a method of producing it, and more particularly to a biochemical analysis unit used for analyzing substances derived from a living organism bound with the spot like specific-binding substances and a method of the producing thereof.

2. Description Related to the Prior Art

Recently, in biology and a medical science studies of genes are progressed. In order to analyze the genes, a radioactive labeling substance is applied as a labeling substance to a substance derived from a living organism. Thereafter the substance derived from the living organism emits a radioactive ray.

A stimulable phosphor sheet is to the substance derived from the living organism so as to absorb, store and record energies of the radioactive ray. Thus the stimulable phosphor sheet is stimulated by an electromagnetic wave having a specified wavelength. Thereafter, the stimulable phosphor can release stimulated emission into an emitted light.

In order to analyze the genes, an autoradiographic analyzing system, as known in Japanese Patent Publications No. 1-70884, 1-70882, 4-3962, is used for detecting the radioactive ray emitted from a stimulable phosphor sheet.

The autoradiographic analyzing system has merits. Unlike a system in which a photographic film is used, in the autoradiographic analyzing system, development of a chemical processing is not necessary. Further, it is possible to reproduce a desired image by effecting image processing on the obtained image data and carry out quantitative analysis by using a computer.

On the other hand, a fluorescent analyzing system is known. In the fluorescent analyzing system, a fluorescent substance is applied as the labeling substance to the substance derived from the living organism. With the fluorescent analyzing system, it is possible to study genetic sequence, the expression level of a gene, routs of metabolism, absorbance, and discharge, and to separate or identify proteins, or estimates the molecular weight or properties of the proteins or the like. As the fluorescent analyzing system, there are, for example, a western blotting method, southern blotting method and the like. In the fluorescent analyzing system, a DNA probe, which is complement to DNA containing a target gene labeled by the labeling substance, is hybridized with DNA on a transfer support. The DNA labeled by the labeling substance is combined with enzyme such that the enzyme may contact a fluorescent substance. The fluorescent substance is excited by a stimutating light to emit fluorescence, and the fluorescence is detected to produce an image and the distribution of a target DNA on the transfer support. There is a merit of the fluorescent analyzing system in which a genetic sequence or the like can be easily detected without using radioactive labeling substances.

Similarly, there is known a chemiluminescence detecting system. In the chemiluminescence detecting system is used the substance derived from a living organism that is labeled with a chemiluminescent labeling substance. The chemiluminescent labeling substance generates chemiluminescence when it contacts a chemiluminescent substrate. The chemiluminescence is detected in the wavelength of visible light to reproduce an image of the chemiluminescence on a displaying means such as a CRT or a recording material such as a photographic film. Thereby, information relating to the high molecular substance is obtained such as genetic information.

Further, a micro-array analyzing system has been recently developed for analyzing a protein such as a nucleic acid, or fragments thereof. The micro-array analyzing system comprises following steps:

(1) using a spotting device to drop specific binding substances at different positions on a surface of a carrier such as a slide glass plate, a membrane filter or the like. The specific binding substances can bind with the substance derived from a living organism such as a hormone, tumor marker, enzyme, antibody, antigen, abzyme, other protein, a nucleic acid, cDNA, DNA, RNA, or the like, whose sequence, base length, composition and the like are known;

(2) forming thereby independent spots of the specific binding substance;

(3) binding or hybridizing, in using a hybridization method, the specific binding substances with the substances which are derived from a living organism and labeled with the labeling substance such as the fluorescent substance, a dye or the like, so as to produce a micro-array;

(4) irradiating the micro-array with a stimulating ray;

(5) photoelectrically detecting light such as the fluorescence emitted from the labeling substances to generate biochemical analysis data; and (6) analyzing the biochemical analysis data.

The micro-array analyzing system has a merit in that substances derived from a living organism can be analyzed in a short time as many sorts of specific binding substances are spotted at different positions on a carrier such as a slide glass plate at high density, and further hybridized with the substance from a living organism and labeled with the labeling substances.

Note that, in the micro-array analyzing system, a micro filtration membrane is used as the biochemical analysis unit for removing particles and bacteria. A method of producing the micro filtration membrane is disclosed in Japanese Patent Laid-open Publications No. 48-40050 and 58-37842.

Further, a macro-array analyzing system has been recently developed for analyzing a protein such as a nucleic acid, or fragments thereof. The macro-array analyzing system comprises following steps:

(1) using a spotting device to drop specific binding substances at different positions on a surface of a carrier such as a slide glass plate, a membrane filter or the like. The specific binding substances can bind with the substance derived from the living organism such as a hormone, tumor marker, enzyme, antibody, antigen, abzyme, other protein, a nucleic acid, cDNA, DNA, RNA, or the like, whose sequence, base length, composition and the like are known;

(2) forming thereby independent spots of the specific living substances;

(3) binding or hybridizing, in using a hybridization method, the specific binding substances with the substances which are derived from a living organism and labeled with the radioactive labeling substances, so as to produce a macro-array;

(4) superposing the macro-array and a stimulable phosphor sheet formed with a stimulable phosphor layer;

(5) exposing the stimulable phosphor layer to radioactive labeling substance;

(6) irradiating the stimulable phosphor layer with a stimulating ray to excite the stimulable phosphor;

(7) photoelectrically detecting the stimulated emission released from the stimulable phosphor to generate the biochemical analysis data; and (8) analyzing the biochemical analysis data.

In the macro-array analyzing system, when the stimulable labeling substances are exposed to the radioactive labeling substances, an electron beam (β-ray) released from the radioactive labeling substance are scattered in the carrier to impinge on a region in the stimulable phosphor layer. However, the radiation energy of the radioactive labeling substances is very large. Accordingly, the electron beams are scattered and mixed with the other electron beams emitted from the neighboring spots and then impinge on the region of the stimulable phosphor layer. Thus a noise is generated in a biochemical analysis data to make the accuracy of the biochemical analysis lower when the substances from the living organism is analyzed by quantifying the radiation amount of each spot. The accuracy of biochemical analysis is markedly degraded when spots are disposed closely to each other at high density.

Further, in the fluorescent analyzing system and the chemiluminescence detecting system, there is a similar problem. The fluorescence and the chemiluminescence are scattered in the carrier such as the membrane filter. Furthermore, the fluorescence and the chemiluminescence emitted from any particular spots is scattered and mixed with chemiluminescence or the fluorescence emitted from the neighboring spots. Accordingly, a noise is generated in the biochemical analysis data.

SUMMARY OF THE INVENTION

An object of the present invention is to provide a biochemical analysis unit and a method of producing it which prevents a generation of a noise in a biochemical analysis data.

In order to achieve the object, a biochemical analysis unit has an absorptive membrane formed of absorptive materials and a plate member formed of a shielding material which can shield at least one of a radioactive ray and a light. In the plate member, plural through-holes are formed. The absorptive membrane covers a first surface of the plate member and a part of the absorptive membrane is supplied in the through-holes. Thus the part appears from the through-holes in a second surface of the plate member to form absorptive regions in the second surface that are surrounded by a plate member.

A method of producing the biochemical analysis unit comprises steps of pressing the plate member on to the absorptive membrane and supplying thereby a part of the absorptive membrane in the through-holes to form the absorptive regions.

In the absorptive regions, specific binding materials are absorbed. The specific binding materials can specifically bind with substances derived from a living organism that are labeled by at least one of labeling substances. As the labeling substances there are radioactive labeling substances, fluorescent substances and chemiluminescent labeling substances. The radioactive labeling substances emit a radioactive ray, and the fluorescent substances and the chemiluminescent labeling substance can emit a fluorescence and a chemiluminescence as the light.

Another biochemical analysis unit has an absorptive membrane formed of the absorptive material and a shielding area formed on the absorptive membrane. The shielding area contains metal colloids particles for shielding the radioactive ray and the light. On a surface of the absorptive membrane, plural absorptive regions are also formed.

Such a biochemical analysis unit is produced through covering parts of a surface of the absorptive membrane with a cover member. In this situation, a solution containing metal colloids particles is provided on other parts of the absorptive membrane. The solution penetrates in the other parts. Thereby the other parts become to the absorptive regions.

Further, a biochemical analysis unit may include the base plate and absorptive regions which are formed on both surfaces of the base plate. In the plate member, plural through-holes are formed. In the through-holes, there are absorptive materials to form the absorptive regions. In order to provide the absorptive materials in the through-holes, a solution of the absorptive materials may be doped on a surface of the plate member. Further, a dispenser may be also used.

Furthermore, a biochemical analysis unit may have a pair of the plate members which are superposed on each other. In this case the absorptive regions are formed on outer surfaces of the plate members.

According to the invention, the specific binding substances are selectively absorbed in each of the absorptive regions, and therefore do not penetrate in the other absorptive regions. In this situation the specific binding substances are bound with the substances derived from the living organism that are labeled with the labeling substances for generating a radioactive ray and a light to be measured. Therefore, the radioactive ray and the light do not diffuse, and in their data there is no noise. Accordingly the analysis of the data can be more accurately carried out. Further, the number of the absorptive regions in a unit size is large. The specific binding substances can be applied closer in the biochemical analysis unit.

Especially, when the data of the radioactive ray is obtained, the radioactive ray emitted from the respective absorbing regions does not diffuse. When an image of the radioactive ray is formed by using an autoradiography, noises in the image become smaller.

In a specific enhancement, the biochemical analysis unit has more than 10 absorptive regions.

Even more specifically, the biochemical analysis unit has more than 1000 absorptive regions.

Even more specifically, the biochemical analysis unit has more than 10000 absorptive regions.

In another specific enhancement, each of the absorptive regions has a size less than 5 mm$^2$.

More specifically, each of the absorptive regions has a size less than 1 mm$^2$.

Even more specifically, each of the absorptive regions has a size less than 0.1 mm$^2$.

In yet another specific enhancement, the averaged density of the number of said absorptive regions is more than 10/cm$^2$.

More specifically, the averaged density of the number of said absorptive regions is more than 1000/cm$^2$.

Even more specifically, the averaged density of the number of said absorptive regions is more than 10000/cm$^2$.

BRIEF DISCRIPTION OF THE DRAWINGS

The above objects and advantages of the present invention will become easily understood by one of ordinary skill in the art when the following detailed description would be read in connection with the accompanying drawings:

FIG. 49 is a diagrammatic view illustrating another situation for forming the biochemical analysis unit of the sixth embodiment;

PREFERRED EMBODIMENTS OF THE INVENTION

Figure 1A:
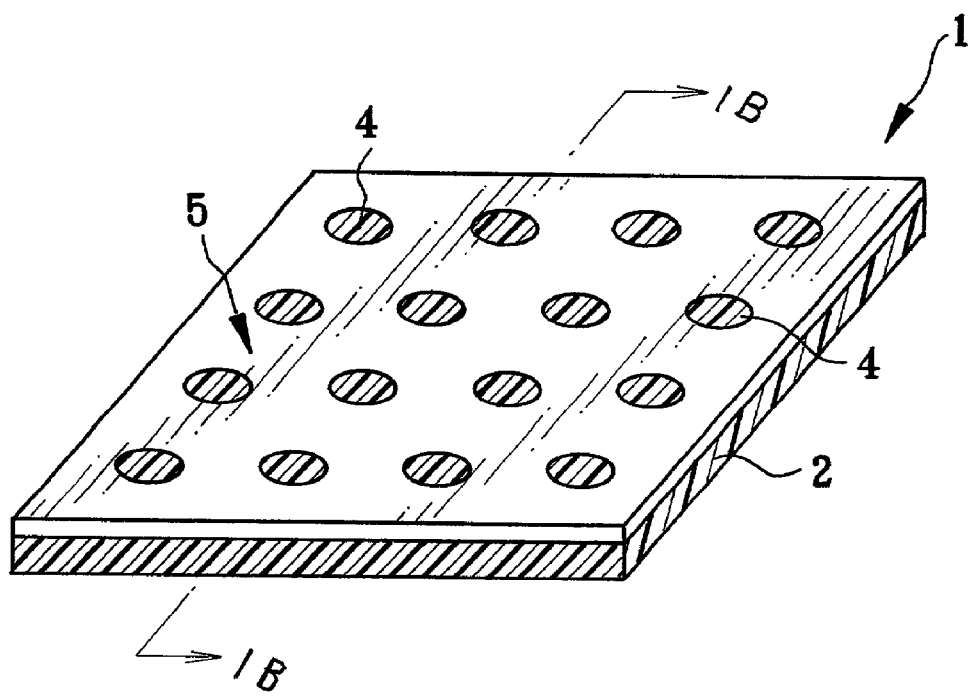
FIG. 1A is a perspective view of a biochemical analysis unit of the first embodiment of the present invention.
Figure 2:
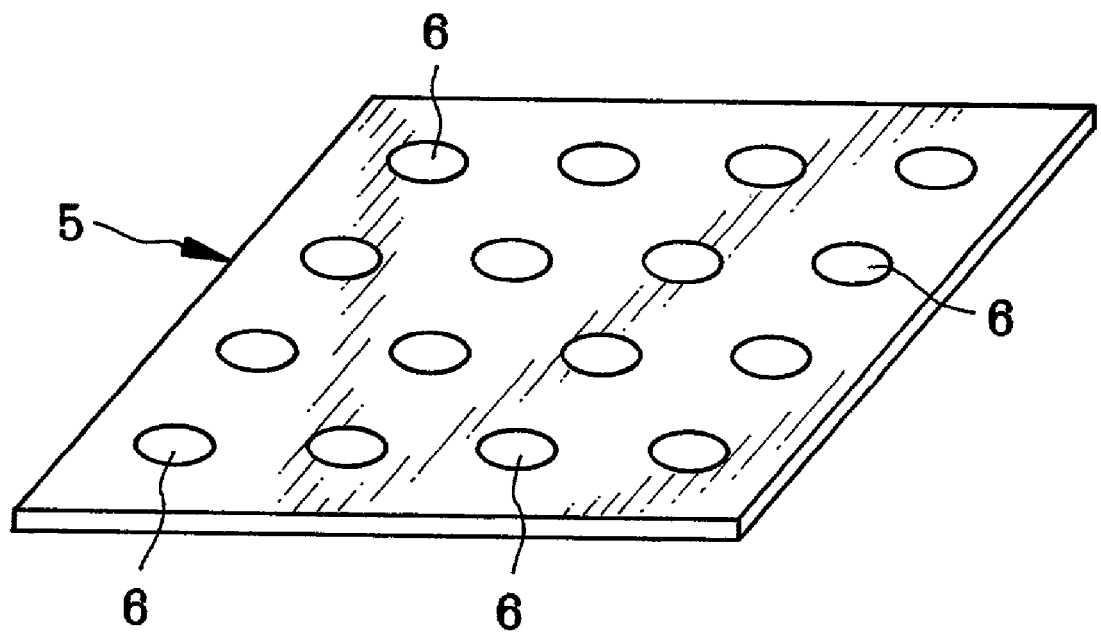
FIG. 2 is a perspective view of a base plate of the biochemical analysis unit in FIG. 1A.

In FIG. 1A, a biochemical analysis unit 1 includes a base plate 5 formed of aluminum and an absorptive material 2 formed of nylon-6 which can be used for forming a membrane filter. On the absorptive material 2, absorptive regions 4 having a nearly circular-shape are formed in a regular pattern. As shown in FIG. 2, in the base plate 5 throughholes 6 are formed, and the absorptive regions 4 are fitted in the through-holes 6 when the base plate 5 is pressed onto the absorptive material 2. Note that in the embodiment the number of the absorptive regions 4 is about 10000 and each of them has a size of about 0.01 mm$^2$. A density thereof is 5000/cm$^2$.

Figure 1B:
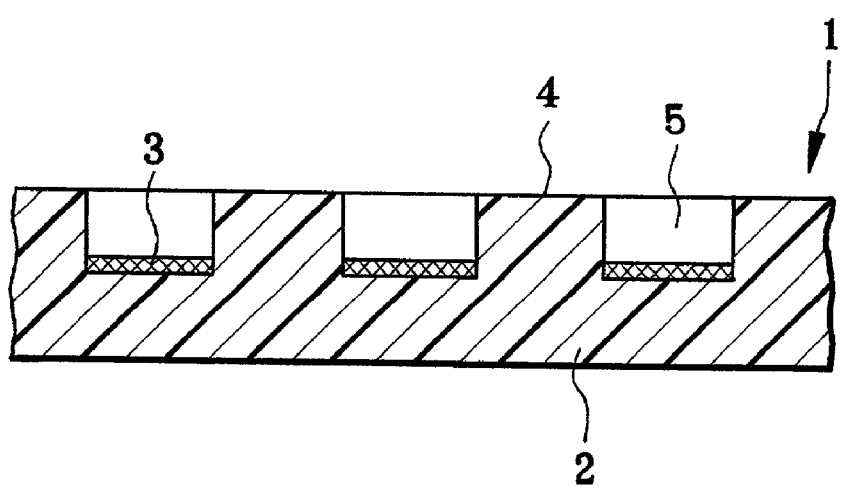
FIG. 1B is a cross-sectional view taken along a line 1B—1B in FIG. 1A.

In FIG. 1B, an adhesive agent 3 is applied on a rear face of the base plate 5. Therefore the base plate 5 is adhered with the absorptive material 2 so as to increase an endurance of the biochemical analysis unit 1. Further, the absorptive region 4 and the aluminum sheet 5 form a flat surface after adhering the base plate 5 to the absorptive material 2.

Figure 3:
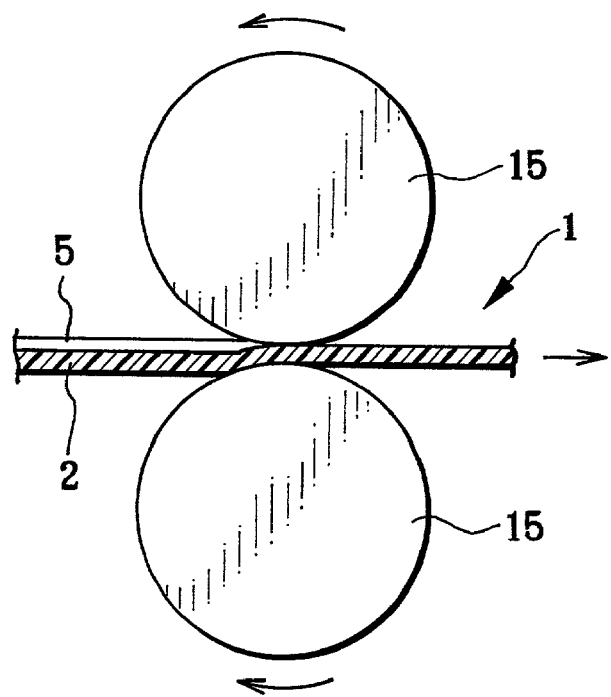
FIG. 3 is a cross-sectional view illustrating a situation in which the biochemical analysis unit is formed by using a pair of press rollers.

In FIG. 3, the biochemical analysis unit 1 is produced with a calendar roller 15 included in a device for producing the biochemical analysis unit 1. Before pressed by the calendar roller 15, the base plate 5 is laid on the absorptive material 2. Then the base plate 5 and the absorptive material 2 are pressed by the calendar roller 15 while the absorptive regions 4 on the absorptive material 2 are fitted into the through-hole 6 of the base plate 5. Note that the absorptive material 2, as formed of nylon-6 for forming membrane filter, has a lot of extremely small holes. The holes are however disappeared by pressing the absorptive material 2 onto the base plate 5.

Figure 4:
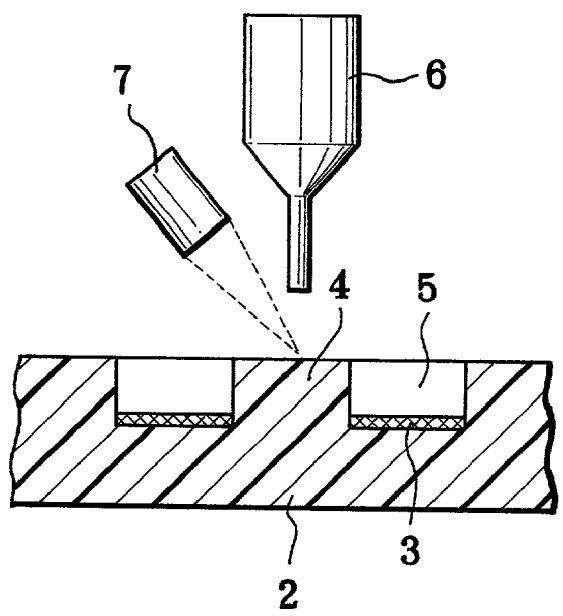
FIG. 4 is a cross-sectional view illustrating a positional relation between a spotting device and the biochemical analysis unit.

As shown in FIG. 4, when a biochemical analysis is carried out, a plurality of cDNA whose sequences are known but different from each other are spotted as specific binding substances by using a spotting device on the absorptive region 4. The spotting device includes an injector 6 and a CCD camera 7. The CCD camera 7 is used for inspecting the absorptive region 4 on which the cDNA is spotted. When a tip end portion of the injector 6 confronts to a center of the absorptive region 4, the cDNA is spotted at an accurate position on the absorptive region 4.

Further, U.S. Pat. No. 5,807,522 describes a method for spotting the specific binding substances to the absorptive regions, in which the specific binding substances are applied to a pin. Furthermore the specific binding substances may be jetted onto the absorptive regions 4.

As the specific binding substances, poly-nucleotides and oligonucleotide are used; for example, cDNA, parts of cDNA, poly-nucleotide of PCR sub-production produced in PCR method such as EST, and the synthetic oligonucleotide. Further there may be artificial nucleus acid, peptide nucleus acid (PNA), and their derivatives. The artificial nucleus acid is produced by transform the phosphodiester bound of the DNA into the peptide bound. Further there are substances which specifically bounds with hormones, tumor markers, enzymes, antibodies, antigens, abzyme, other proteins, nucleic acids, DNA, RNA and the like.

The DNA of the specific binding substances is bound with DNA and RNA. The PNA, the antigene and avidine of the specific binding substances are bound with the PNA, the antibody, and biotine respectively.

Note that instead of the inspecting of the absorptive region 4 a positional relation between the injector 6 and the absorptive region 4 may be previously detected for spotting the cDNA. In this case, the injector 6 and the biochemical analysis unit 1 are relatively moved in a predetermined speed.

In the biochemical analysis unit 1, an area between the absorptive regions 4 on the absorptive material 2 is entirely covered with the base plate 5. Accordingly, the specific binding material on the absorptive region 4 does not flow onto the area between the absorptive regions 4. Further, as the extremely small holes of the absorptive material 2 are disappeared by pressing onto the base plate 5, the specific binding material is absorbed only in the absorptive regions 4.

Figure 5:
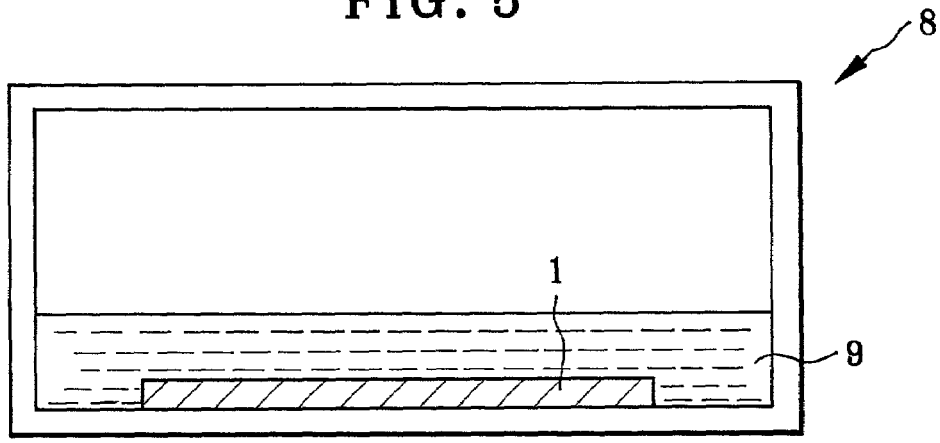
FIG. 5 is a cross-sectional view of a hybridization vessel.

As shown in FIG. 5, a hybridization vessel 8 is formed cylindrically and contains a hybridization solution 9. In the hybridization solution 9 there is one or more of substances derived from a living organism which are labeled with a labeling substance.

When the specific binding substance such as cDNA is selectively labeled with one of radioactive labeling substances, the substance derived from a living organism is labeled with the radioactive labeling substance in the hybridization solution 9.

When the specific binding substance such as cDNA is selectively labeled with one of chemiluminescent labeling substances, the substance derived from the living organism is labeled with the chemiluminescent labeling substance in the hybridization solution 9.

Further, when the specific binding substance such as cDNA is selectively labeled with one of fluorescent substances, the substance derived from the living organism is labeled with the fluorescent substance in the hybridization solution 9.

When the hybridization is performed, the biochemical analysis unit 1 is inserted in the hybridization vessel 8.

Thus, the specific binding substances in the absorptive region 4 are selectively hybridized with the substances from the living organism that are labeled with the radioactive labeling substances, the chemiluminescent labeling substances or the fluorescent substances.

Accordingly, the following data are recorded on the absorptive region 4: a radioactive data of the radioactive labeling substances; a chemiluminescent data of the chemiluminescent labeling substance; and a fluorescent data of the fluorescent substance.

The radioactive data is transmitted on a stimulable phosphor sheet 10 (see FIG. 6), and read from the stimulable phosphor sheet 10 by a scanner (see FIG. 8) so as to generate a biochemical analysis data.

Further, the fluorescent data recorded on the absorptive region 4 are read by the scanner to generate the biochemical analysis data. Furthermore, the chemiluminescent data recorded in the absorptive region 4 are read by a data producing system (see FIG. 16) to generate the biochemical analysis data.

Figure 6:
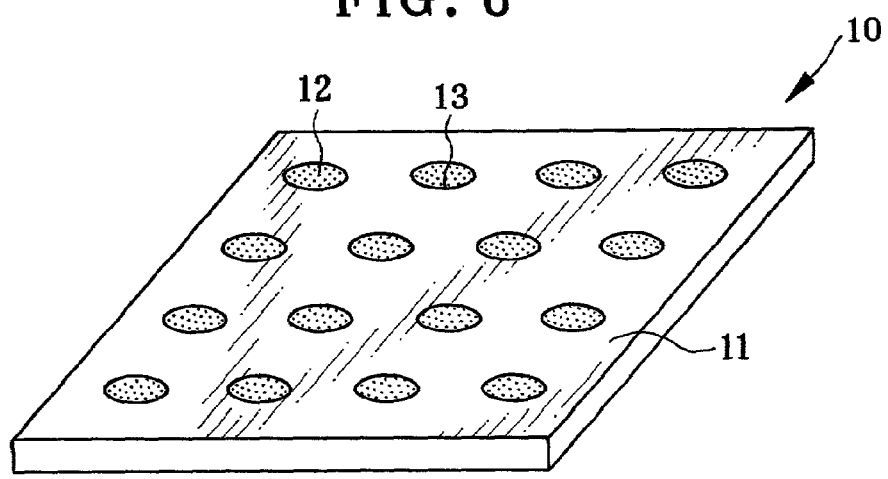
FIG. 6 is a perspective view of a stimulable phosphor sheet.

As shown in FIG. 6, the stimulable phosphor sheet 10 includes a supporter 11. On a surface of the supporter 11 is formed plural recesses 13 in the same regular pattern as that of the through-holes 6 formed on the biochemical analysis unit 1. The recesses 13 are dot-like and substantially circular shaped. In the recesses 13, stimulable phosphor substances are provided to form a stimulable phosphor layer region 12. Thereby the stimulable phosphor layer region 12 has such a thickness that a surface of the supporter 11 becomes flat.

In this embodiment, the supporter 11 is formed of stainless capable of reducing radiation energy, and the stimulable phosphor layer region 12 is formed on the supporter 11 so as to have the same diameter as the absorptive region 4.

Figure 7:
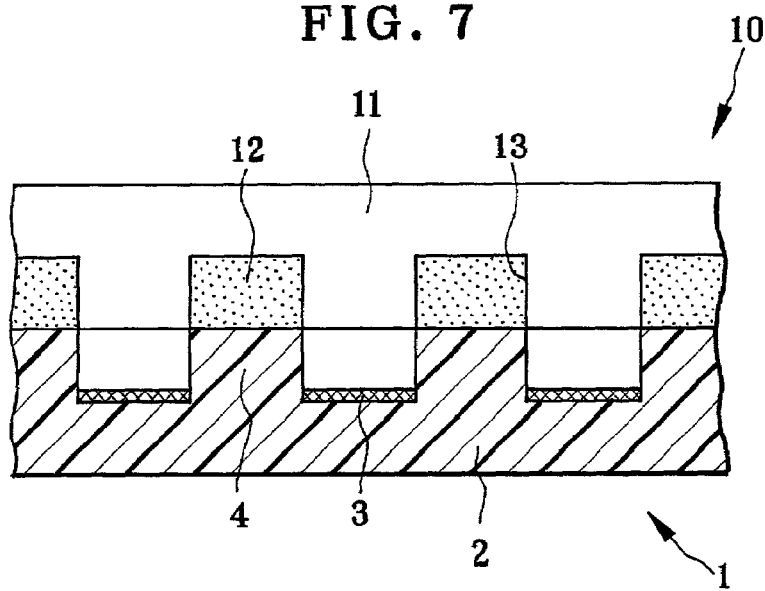
FIG. 7 is a cross-sectional view illustrating a situation when the stimulable phosphor sheet is superposed on the biochemical analysis unit.

As shown in FIG. 7, the stimulable phosphor sheet 10 is superposed on the biochemical analysis unit 1 by exposure such that the absorptive regions 4 may confront to the stimulable phosphor layer region 12.

In this embodiment, since the absorptive material 2 is pressed onto the base plate 5, the biochemical analysis unit 1 is hardly stretched and shrunk even if it is subjected to liquid processing such as hybridization. Therefore, the absorptive regions 4 can correctly confront to the stimulable phosphor layer regions 12.

Thereby the radioactive labeling substance on the absorptive region 4 emits electron beam only onto the confronting stimulable phosphor layer regions 12 so as to carry out the exposure. The electron beams are not scattered on the absorptive material 2 as the base plate 5 attached thereto has an effect of reduction of the density of the radioactive ray. Namely, the base plate 5 prevents the electron beam from tending to the neighboring stimulable phosphor layer regions 12.

Thus, the radioactive data are recorded in the stimulable phosphor layer regions 12.

Note that the substances derived from the living organism may be labeled with the radioactive labeling substances and only one of the fluorescent substances and the chemiluminescent labeling substances. Further, the substances derived from the living organism may be bound to the specific labeling material through the antigen-antibody reaction, the receptor-ligand reaction or the like instead of hybridization.

Figure 8:
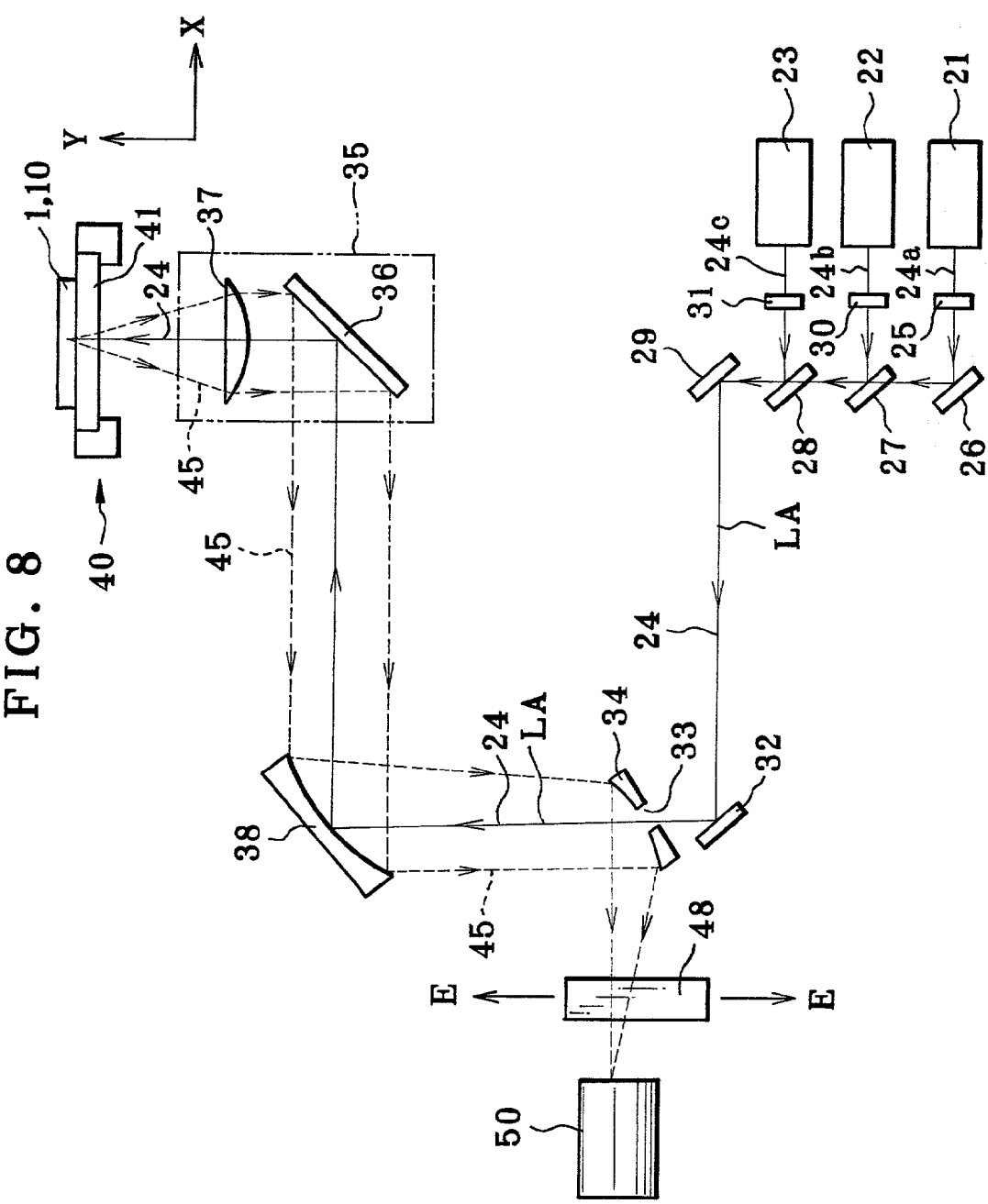
FIG. 8 is a diagrammatic plan view of a scanner.

In FIG. 8, the scanner can read the radiation data from the stimulable phosphor layer regions 12 and the fluorescent data from the absorptive regions 4 so as to generate the biochemical analysis data. The scanner includes first, second and third laser sources 21, 22, 23. The first laser source 21 is constructed of a semiconductor laser, and projects a laser beam 24a having wavelength of 640 nm. The second and third laser sources 22, 23 are constructed of second harmonic generation elements and projects a laser beam 24b having wavelength of 532 nm and a laser beam 24c having wavelength of 473 nm, respectively.

The scanner includes further first and second diachronic mirrors 27, 28 which selectively reflect the laser beams 24a, 24b, and 24c.

A laser beam 24a emitted from the first laser 21 is formed through a collimator lens 25 into a parallel beam, and is reflected by a mirror 26. A first diachronic mirror 27 and the second diachronic mirror 28 transmit the laser beam 24a. A laser beam 24b emitted from the second laser 22 is formed through a collimator lens 30 to be a parallel beam, and reflected by the first diachronic mirror 27. Then, the second diachronic mirror 28 transmits also the laser beam 24b. A laser beam 24c emitted from the third laser 23 passes through a collimator lens 31 to be a parallel beam, and reflected by the second diachronic mirror 28.

Thereafter, each of the laser beams 24a, 24b, 24c passes as an exiting beam 24 on an optical axis L in a light path and is reflected by mirror 29 and 32.

Downstream of the mirror 32, a perforated mirror 34 is disposed in the optical path. In a center of the perforated mirror 34 is formed a hole 33 through which the exiting beam 24 passes. Then the exiting beam 24 is reflected by a concave mirror 38 and enters into an optical head 35.

The optical head 35 includes a mirror 36 and an aspherical lens 37. After entering into the optical head 35, the exiting beam 24 is reflected by the mirror 36, and condensed by the aspherical lens 37 onto the stimulable phosphor sheet 10 or the biochemical analysis unit 1, which is placed on a glass plate 41 of the stage 40. Thereby, the biochemical analysis unit 1 is placed such that each of the absorptive region 4 and the stimulable phosphor layer regions 12 may be scanned.

Figure 14:
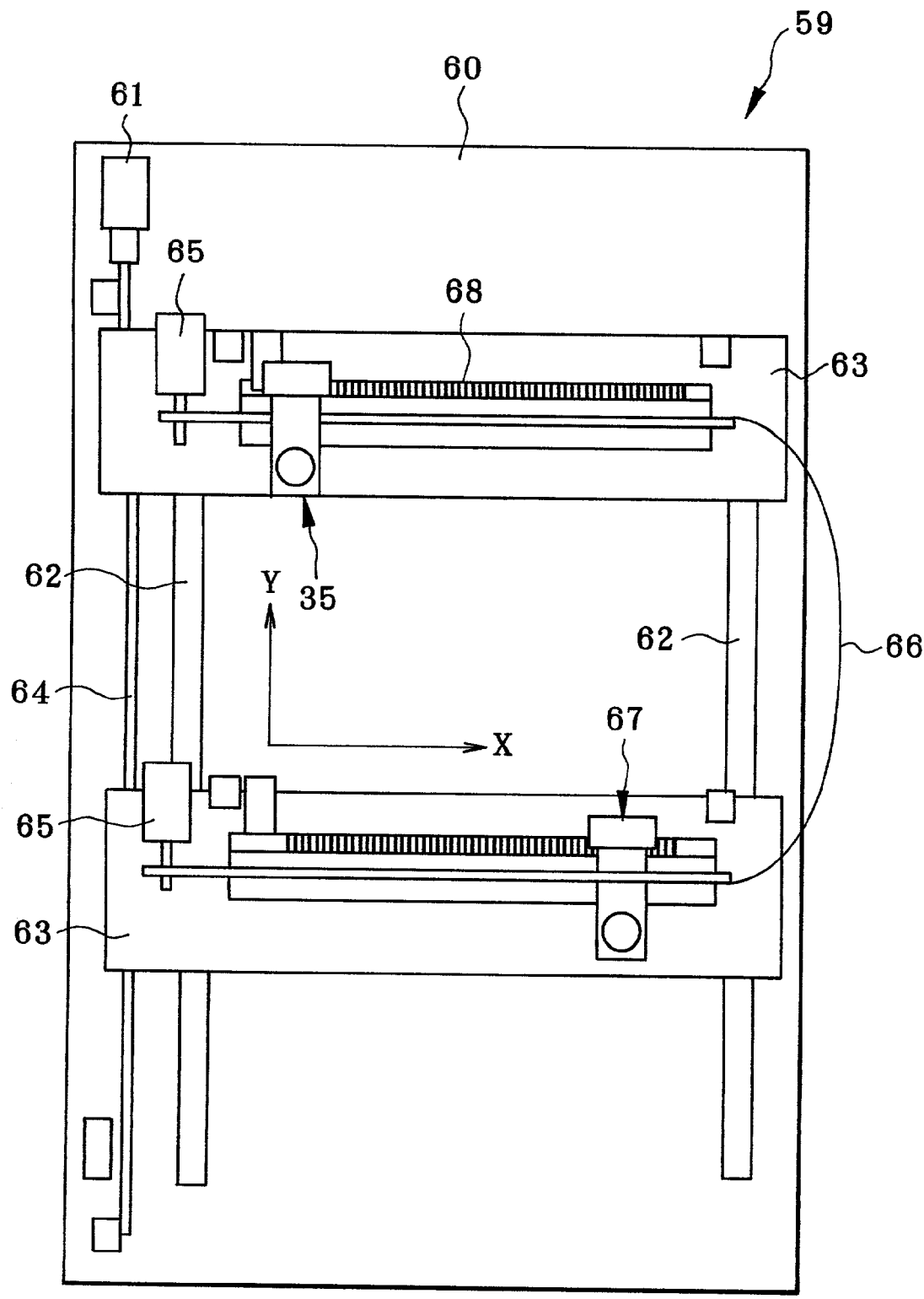
FIG. 14 is a plan view of a optical head of the scanner.

The optical head 35 is movable in a main-scanning direction X and a sub-scanning direction Y by a scanning mechanism 59 (see FIG. 14). Accordingly, all of stimulable phosphor layer regions 12 and the absorptive regions 4 are scanned.

When the exiting beam 24 impinges on the stimulable phosphor layer region 12, the stimulable phosphor in the stimulable phosphor layer region 12 is excited to release stimulated emission as an emission light 45. On the other hand, when the exiting beam 24 impinges on the biochemical analysis unit 1, a fluorescent dye or the like contained in the absorptive region 4 is excited to release a fluorescence as the emission light 45.

Then the emission light 45 is formed to a parallel light beam by the aspherical lens 37 and reflected by the mirror 36. Thereafter, the emission light 45 is reflected to the perforated mirror 34 by the concave mirror 38. When reflecting on the perforated mirror 34, the emission light 45 is focused onto the photomultiplier 50. Thereby the emission light 45 passes through a filter unit 48 in which a part of the emission light 45 having a predetermined wavelength is cut off.

Figure 9:
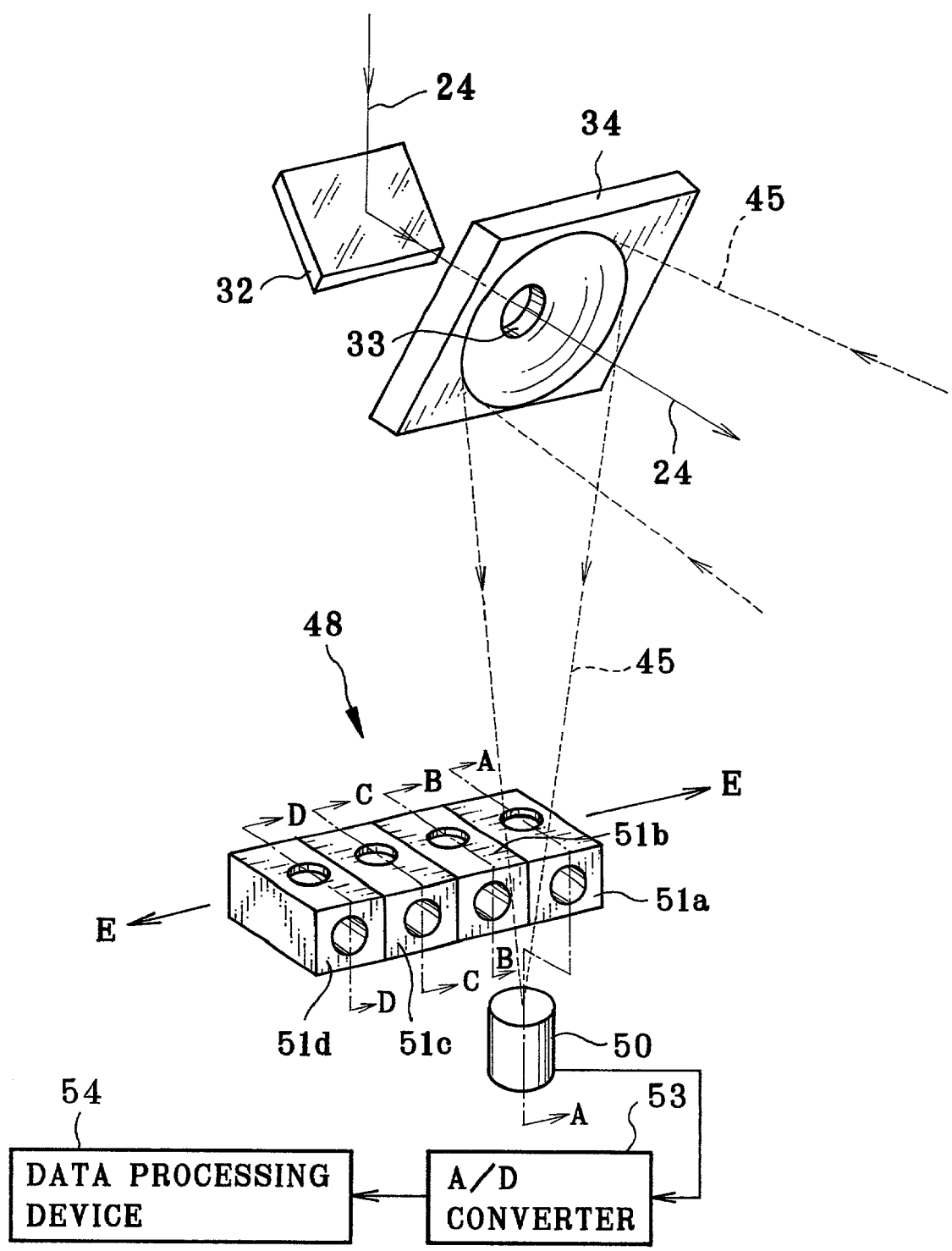
FIG. 9 is a partially enlarged view of the scanner, illustrating a structure of a filter unit.

In FIG. 9, the filter unit 48 includes four filter members 51a, 51b, 51c, 51d and is slidable in left and right direction. The photomultiplier 50 is connected through a A/D converter 53 to a data processing device 54.

Figure 10:
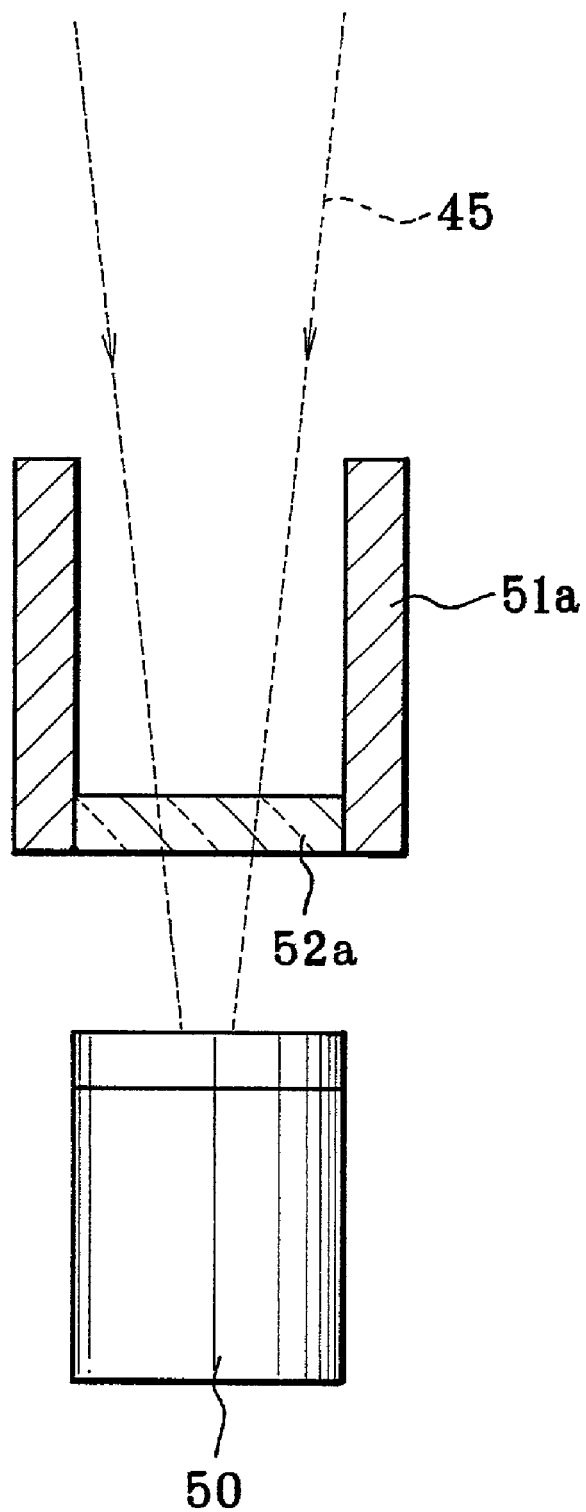
FIG. 10 is a sectional view taken along a line A—A in FIG. 9.

As shown in FIG. 10, the filter member 51a includes a filter 52a. The filter 52a is used for reading the fluorescent data when the laser beam 24a from the first laser 21 excites the fluorescent substances on the absorptive region 4. The filter 52a cuts a light having the wavelength of 640 nm and transmits a light having the wavelength more than 640 nm.

Figure 11:
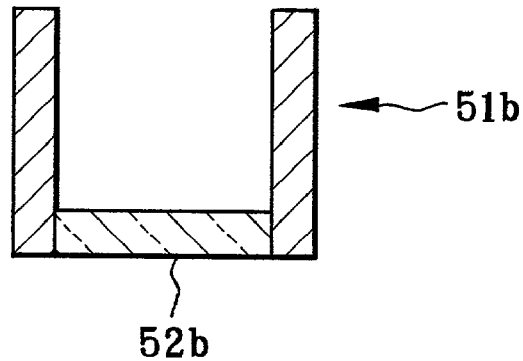
FIG. 11 is a sectional view taken along a line B—B in FIG. 9.

As shown in FIG. 11, the filter member 51b includes a filter 52b. The filter 52b is used for reading the fluorescent data when the laser beam 24b from the first laser 22 excites the fluorescent substances on the absorptive region 4. The filter 52b cuts a light having the wavelength of 532 nm and transmits a light having the wavelength more than 532 nm.

Figure 12:
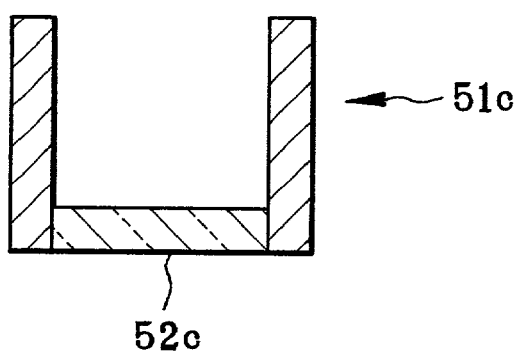
FIG. 12 is a sectional view taken along a line C—C in FIG. 9.

As shown in FIG. 12, the filter member 51c includes a filter 52c. The filter 52c is used for reading the fluorescent data when the laser beam 24c from the first laser 22 excites the fluorescent substances on the absorptive region 4. The filter 52c cuts a light having the wavelength of 473 nm and transmits a light having the wavelength more than 473 nm.

Figure 13:
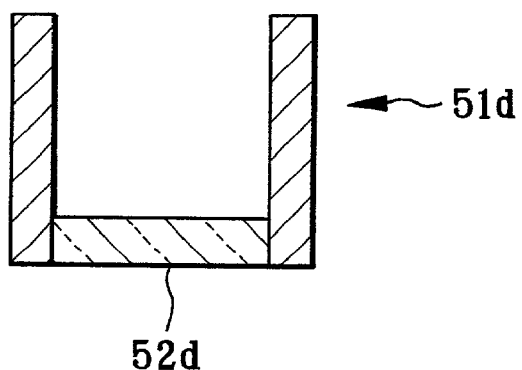
FIG. 13 is a sectional view taken along a line D—D in FIG. 9.

As shown in FIG. 13, the filter member 51d includes a filter 52d. The filter 52d is used for reading the radioactive data when the laser beam 24a from the first laser 21 excites the stimulable phosphor on the stimulable phosphor layer region 12. The filter 52d cuts a light having the wavelength of 640 nm and transmits a light having the wavelength in a region of the stimulated emission.

As described above, in accordance with the biochemical analysis data, one of the filter members 51a, 51b, 51c, 51d is selected and disposed in front of the photomultiplier 50.

The photomultiplier 50 photoelectrically detects the emission light 45 to generate analog data. The analog data are converted with an A/D converter 53 into digital data, and the digital data are fed to the data processing device 54.

As shown in FIG. 14, the optical head 35 is attached to the scanning mechanism 59. The scanning mechanism 59 includes a board 60 on which a sub-scanning stepping motor 61 and a pair of rails 62 are fixed. The board 60 is provided with a movable plate which can move in the sub-scanning direction Y.

The movable plate 63 is formed with a threaded hole (not shown). In the threaded hole is fitted a threaded rod 64 rotated by the sub-scanning stepping motor 61. On the movable plate 63, a main-scanning stepping motor 65 is provided. The main-scanning pulse motor drives an endless belt 66 at a certain interval. To the endless belt 66 the optical head 35 is attached. Accordingly, when the endless belt 66 is driven, the optical head 35 is moved. Thereby the main-scanning pulse motor 65 drives the endless belt 66 so as to intermittently move the optical head 35 in the main-scanning direction X for a distance between the neighboring absorptive regions 4.

Further, an indication 67 is a linear encoder for detecting a position of the optical head in the main-scanning direction X, and an indication 68 is a slit of the linear encoder 67.

When a line of the scanning is complete, the sub-scanning stepping motor 61 causes to move the movable plate 63 in the sub-scanning direction Y. Thus, the stimulable phosphor layer regions or the absorptive regions are entirely scanned.

Figure 15:
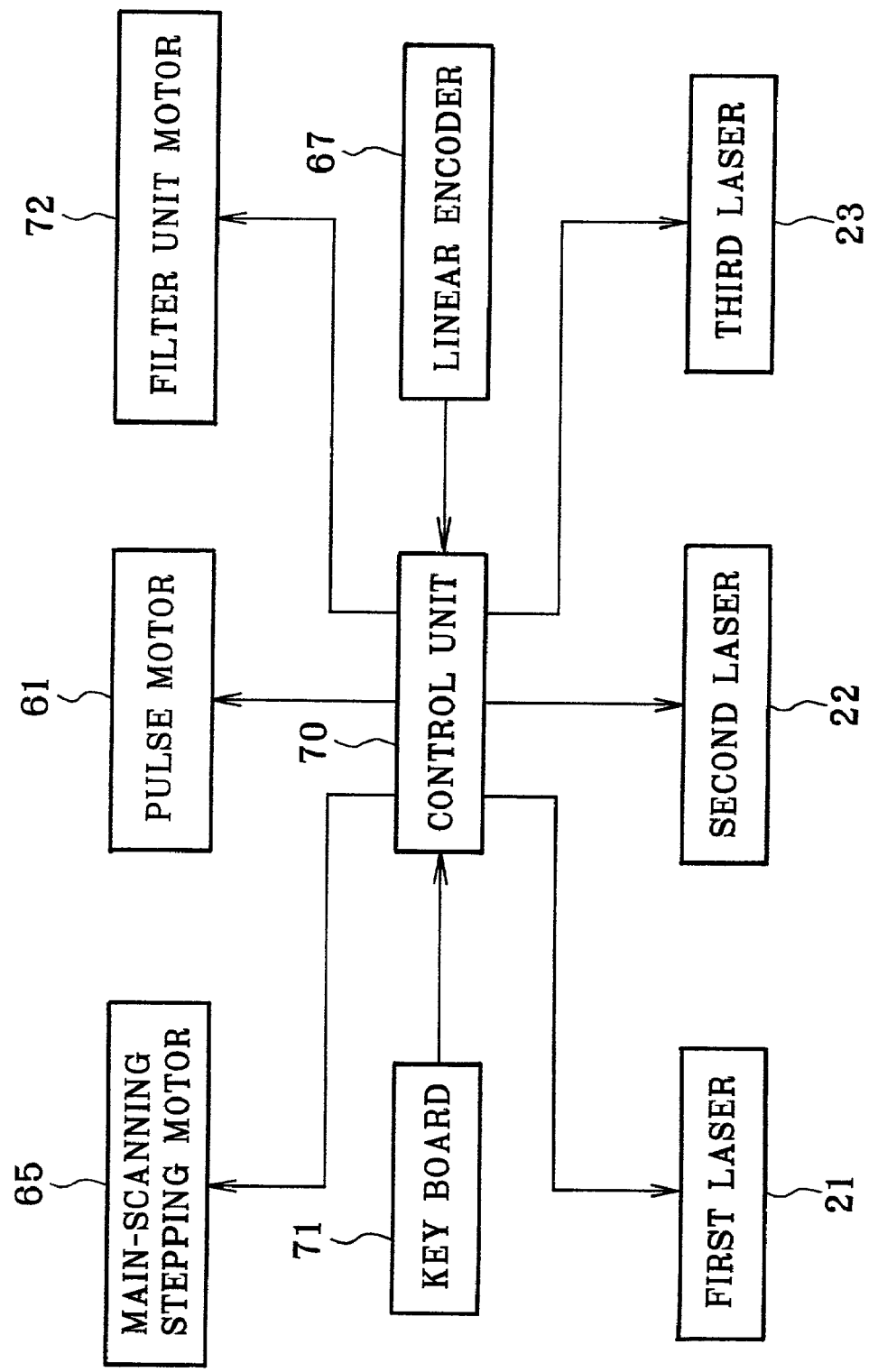
FIG. 15 is a block diagram of a scanner control system.

As shown in FIG. 15, a scanner control system includes a control unit 70 for a whole operation of the scanner, and a scanner input system includes a keyboard 71 which can be operated by an operator and through which various instruction signals can be input. A drive system of the scanner includes the main-scanning stepping motor 65, the sub-scanning stepping motor 61, and the filter unit motor 72 for moving the filter unit 48.

The control unit 70 selectively outputs drive signals to the first laser 21, the second laser 22, the third laser 23, and further send drive signals to a filter unit motor 72. A scanner detecting system includes the photomultiplier 50 and the linear encoder 67.

In the embodiment, the control unit 70 receives a detection signal of positions of the optical head 35. In accordance with the detection signal the control unit 70 controls to set the first, second third lasers 21, 22, 23 in ON/OFF situations.

The scanner described above reads the radioactive data of the radioactive labeling substances from the stimulable phosphor sheet 10 to generate the biochemical analysis data while the stimulable phosphor layer regions 12 of the stimulable phosphor sheet 10 are exposed by the radioactive labeling substances on the absorptive regions 4.

Now an operation for exposure of the stimulable phosphor layer regions is described. The stimulable phosphor sheet 10 is set on the glass plate 41 of the stage 40 such that the stimulable phosphor layer regions 12 may contact to a surface of the glass plate 41. Then, the user inputs an instruction signal through the keyboard 71 to instruct to the control unit 70 that the stimulable phosphor sheet 10 is scanned in the laser beam 24a.

After inputting the instruction signal, the control unit 70 outputs the drive signal to the filter unit motor 72 to move the filter unit 48. Thereby the filter member 51d including the filter 52d is set in the passage of the emission light 45. Thus only the emission light 45 can pass through the filter 52d when it is emitted from the stimulable phosphor substances.

Further, the control unit 70 outputs the drive signal to the main-scanning stepping motor 65 to move the optical head 35 in the scanning direction from an initial position. Then, based on the detection signal of the position of the optical head 35, the control unit 70 determines whether the optical head is correctly positioned so as to illuminate the first stimulable phosphor layer region 12 in the laser beam 24. Thereafter, the control unit 70 outputs to the main-scanning stepping motor 65 a signal for stopping the drive of the main-scanning stepping motor 65, and thereby also send the drive signal to the first laser 21 to drive it for emitting the laser beam 24a having the wavelength of 640 nm.

When the laser beam 24a is emitted from the first laser 21, the first stimulable phosphor layer region 12 is illuminated in the laser beam 24a and excited to emit the stimulous emission as the emission light beam. Thereby, the laser beam 24a may be reflected on the stimulabel phosphor layer region 12 and mixed with the emission light beam. However, the reflected laser beam 24a is cut by the filter 52d of the filter member 51d. Accordingly, the photomultiplier 50 photoelectrically detects only the stimulous emission which can pass through the filter 52d to generate the analog data of the first stimulable phosphor layer region 12.

After the analog data is transformed in the digital data by the A/D converter 53, the digital data is sent to the data processing device 54. Corresponding to receiving the digital data of the data processing device 54, the control unit 70 outputs the drive signal for stopping the drive of the first laser 21, and controls the optical head 35 to move for a distance to the second stimulable phosphor layer regions 12.

Thereafter, when it is ascertained that the second stimulable phosphor layer region 12 may be illuminated in the laser beam, the first laser 21 is driven to project the laser beam 24a, and the second stimulable phosphor layer regions 12 are excited to emit the stimulous emission as the emission light 45. Then, the photomultiplier 50 photoelectrically detects only the stimulous emission which can pass through the filter 52d to generate the analog data of the first stimulable phosphor layer region 12. When the photomultiplier 50 generates the analog data, the first laser 21 is turned OFF and the optical head 35 is moved again.

Thus the scanning of one line on the stimulable phosphor sheet 10 is completely performed by intermittently moving the optical head 35. When ascertaining it the control unit 70 outputs the drive signal to the main-scanning stepping motor 65 to shift in the initial position, and outputs the drive signal to the sub-scanning stepping motor 61 to slide the movable plate 63 for a line in the sub-scanning direction. Then the scanning of the second line is performed.

In repeating the operations above described, the stimulable phosphor sheet 10 is entirely scanned.

The biochemical analysis unit 1 is set on the glass plate 41 of the stage 40. The user inputs an instruction signal through the keyboard 71 to instruct to the control unit 70 that the biochemical analysis unit 1 is scanned in one of the laser beams 24a, 24b, 24c.

After inputting the instruction signal, the control unit 70 determines, based on a table memorized in a memory (not shown), what may be used among the first, second, third lasers 21, 22, 23, and what may be set in the light path among the filters 52a, 52b, 52c, 52d.

For example, Rohdamine is used as the fluorescent substance that can be most effectively excited by the laser beam 24b. The user inputs information thereof through the keyboard 71. Based on the information, the control unit 70 selects the second laser 22 and the filter 52b. Thereby, the drive signal is output to the filter unit motor 72 to move the filter unit 48 such that the filter member 51b including the filter 52b is set in the light path of the emission light 45. Thus only the emission light 45 can pass through the filter.

Further, the control unit 70 outputs the drive signal to the main-scanning stepping motor 65 to move the optical head 35 in the scanning direction from an initial position. Then, based on the detection signal of the position of the optical head 35, the control unit 70 determines whether the optical head 35 is correctly positioned so as to illuminate the first absorptive region 4 in the laser beam 24b. Thereafter, the control unit 70 outputs to the main-scanning stepping motor 65 a signal for stopping the drive of the main-scanning stepping motor 65, and thereby also send the drive signal to the second laser 22 to drive it for emitting the laser beam 24b having the wavelength of 532 nm.

When the laser beam 24b is emitted from the second laser 21, the first absorptive region 4 is illuminated in the laser beam 24b, and the fluorescent substance, Rohdamine, is excited to emit the fluorescence as the emission light beam.

In the biochemical analysis unit 1 of this embodiment, as the base plate 5 is applied to the absorptive material 2, the fluorescent substances on the neighboring absorptive regions 4 is not excited.

Further, the laser beam 24b may be reflected on first absorptive region 4 and mixed with the emission light 45. However, the reflected laser beam 24b is cut by the filter 52b of the filter member 51b. Accordingly, the photomultiplier 50 photoelectrically detects only the stimulous emission emitted by Rohdamine on the first absorptive region 4, which can pass through the filter 52b to generate the analog data of the first absorptive region 4.

After the analog data is transformed in the digital data by the A/D converter 53, the digital data is sent to the data processing device 54. Corresponding to receiving the digital data of the data processing device 54, the control unit 70 outputs the drive signal for stopping the drive of the second laser 22, and controls the optical head 35 to move for a distance to the second absorptive region 4.

Thereafter, when it is ascertained that the second absorptive region 4 may be illuminated in the laser beam 24b, the second laser 22 is driven to project the laser beam 24b, and the second absorptive region 4 is excited to emit the fluorescence as the emission light 45. Then, the photomultiplier 50 photoelectrically detects only the fluorescence which can pass through the filter 52b to generate the analog data of the first absorptive region 4. When the photomultiplier 50 generates the analog data 4, the second laser 22 is turned OFF and the optical head 35 is moved again.

Thus the scanning of one line on the biochemical analysis unit 1 is completely performed by intermittently moving the optical head 35. When ascertaining it, the control unit 70 outputs the drive signal to the main-scanning stepping motor 65 to shift in the initial position, and outputs the drive signal to the sub-scanning stepping motor 61 to slide the movable plate 63 for a line in the sub-scanning direction. Then the scanning of the second line is performed.

In repeating the operations above described, the biochemical analysis unit 1 is entirely scanned.

Note that the scanner is not restricted in the above embodiments. For example, the scanner cannot selectively read the radioactive data, the chemiluminescent data and the fluorescent data, but only one of them. In this case, three scanners are used for reading all of the three data, and in each scanner, the light emitting diode, the filters, the diffusing plate or the like may be omitted.

Further, the optical head 35 may be fixed. In this case, the stage 40 is moved in the main-scanning direction x and the sub-scanning direction y. Furthermore, instead of the photomultiplier 50, CCDs may be arranged in a line or plane.

Figure 16:
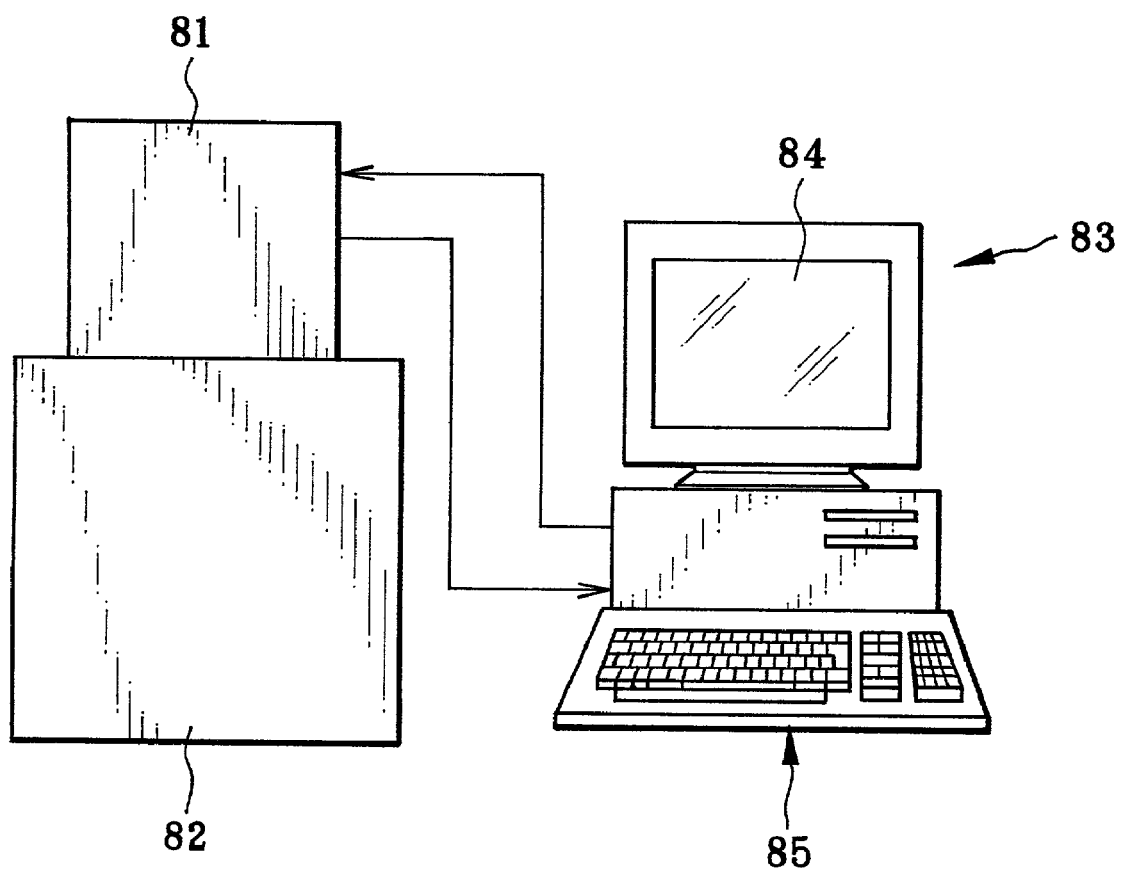
FIG. 16 is a front view of a data producing system.

In FIG. 16, the data producing system includes a cooled CCD camera 81, a dark box 82 and a personal computer 83. The personal computer 83 has a CRT 84 and a keyboard 85.

The data producing system reads the chemiluminescent data of the chemiluminescent labeling substance recorded in the absorptive regions 4 on the biochemical analysis unit 1 to generate the biochemical analysis data. The chemiluminescent labeling substance emits the chemiluminescence when it contact to the chemiluminescent substrate. Note that the data producing system can also read the fluorescence data of the fluorescent substance on the absorptive region 4, such as the fluorescent dye.

Figure 17:
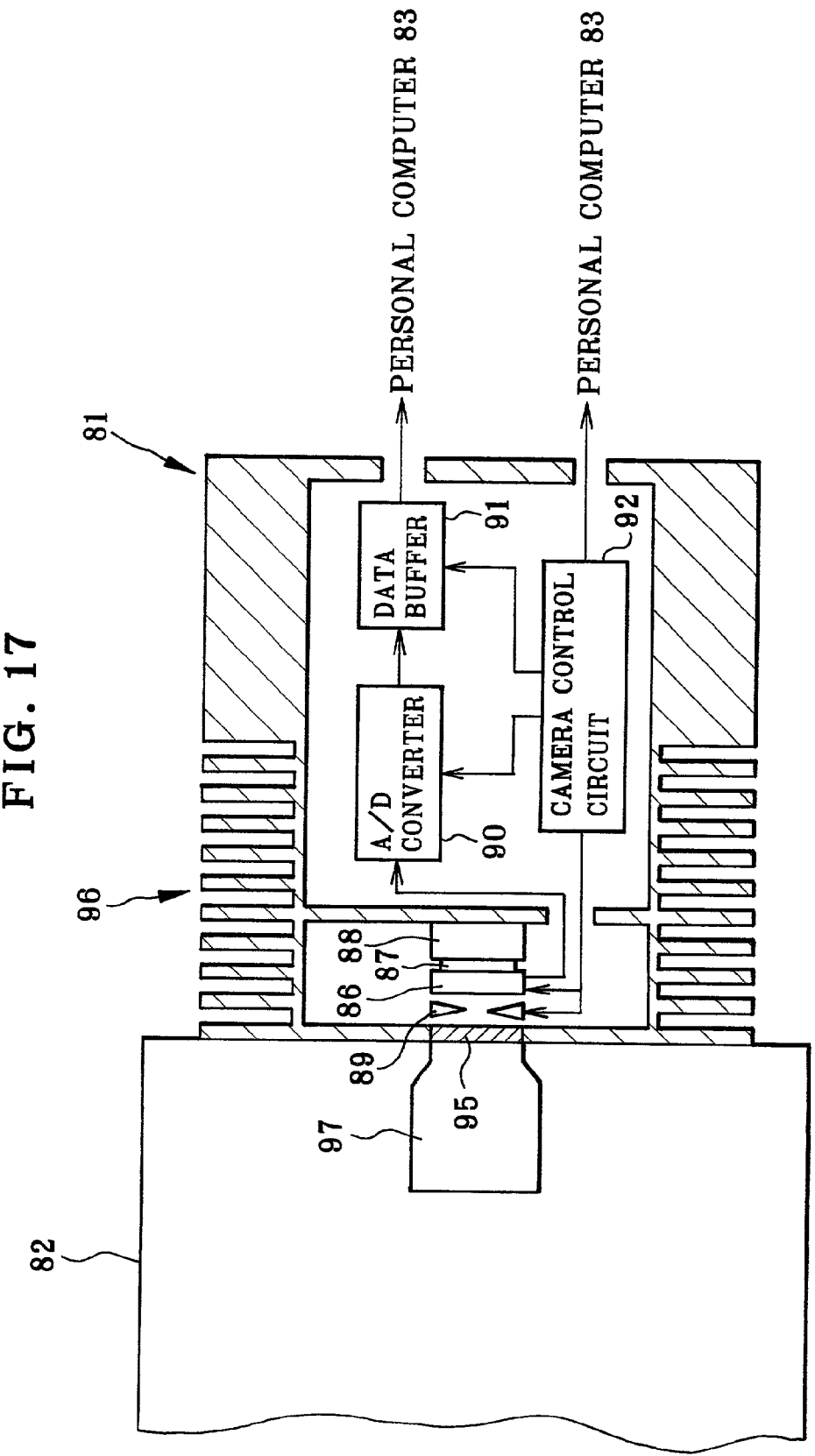
FIG. 17 is a sectional view of a cooled CCD camera of the data producing system.

As shown in FIG. 17, the cooled CCD camera 81 includes a CCD 86, a heat transfer plate 87 made of metal, such as aluminum, a Pelitier element 88 for cooling the CCD 86, a shutter 89 disposed in front of the CCD 86, and A/D converter 90 for converting an analog data into a digital data, a data buffer 91 for temporarily storing the digital data, and a camera control circuit 92 for controlling the operation of the cooled CCD camera 81.

An opening between the dark box 82 and the cooled CCD camera 81 is closed with a glass plate 95. A periphery of the cooled CCD camera 81 is formed with heat dispersion fins 96 over substantially half its length for dispersing heat. In the cark box 82, a camera lens 97 is disposed on the glass plate 95.

Figure 18:
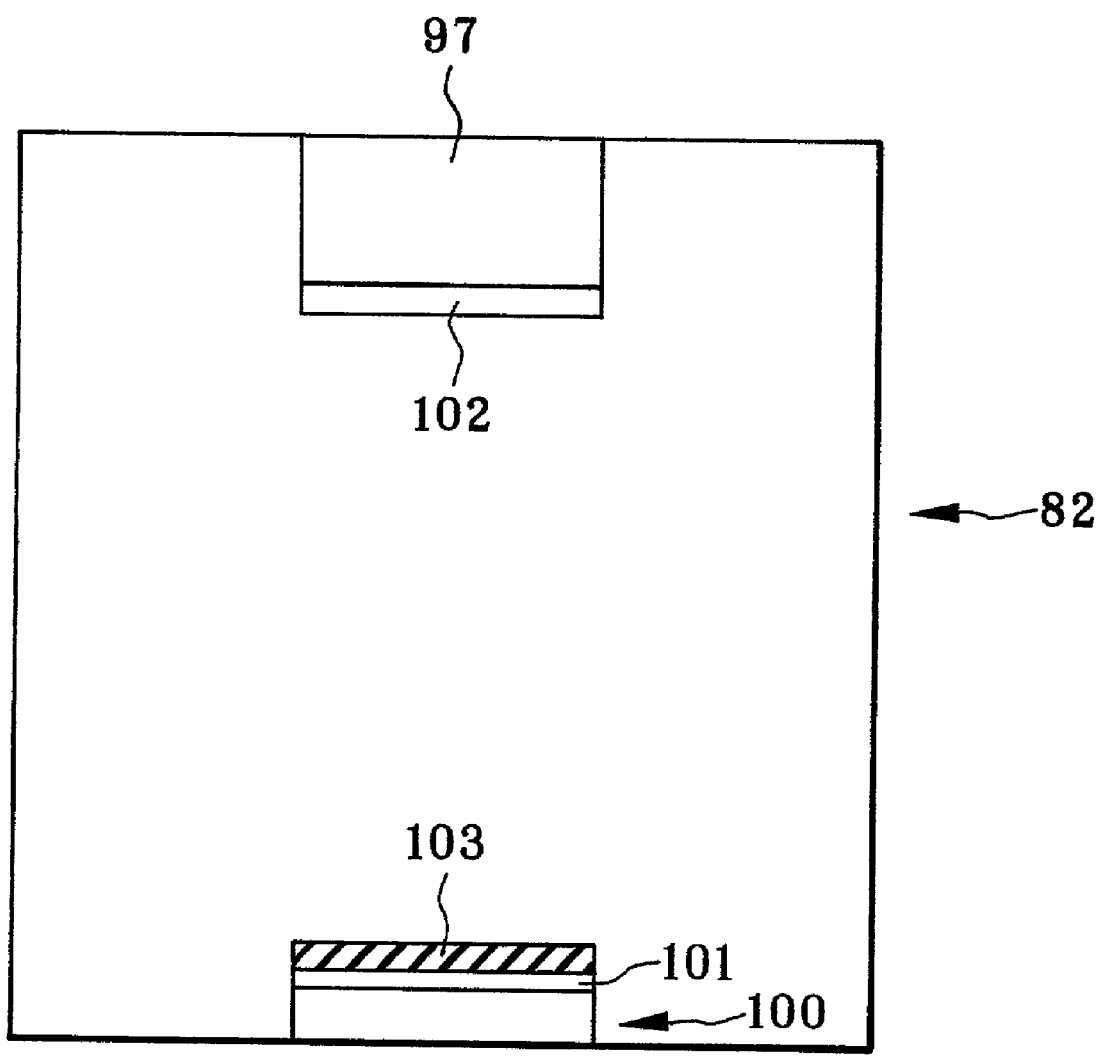
FIG. 18 is a sectional view of a dark box of the data producing system.

As shown in FIG. 18, the dark box 82 is equipped with a light emitting diode 100 for emitting a stimulating ray. The light emitting diode 100 is provided with a filter 101. On an upper surface of the filter 101 is disposed a diffusion plate 103 for superposing the biochemical analysis unit 1 thereon. Through the diffusion plate 103, the biochemical analysis unit 1 can be uniformly irradiated with the stimulating ray. The filter 101 cuts a light having the wavelength not close to that of the stimulating ray. On a front face of the camera lens 97, a filter 102 is provided for cutting a light having the wavelength close to that of the stimulating ray.

Figure 19:
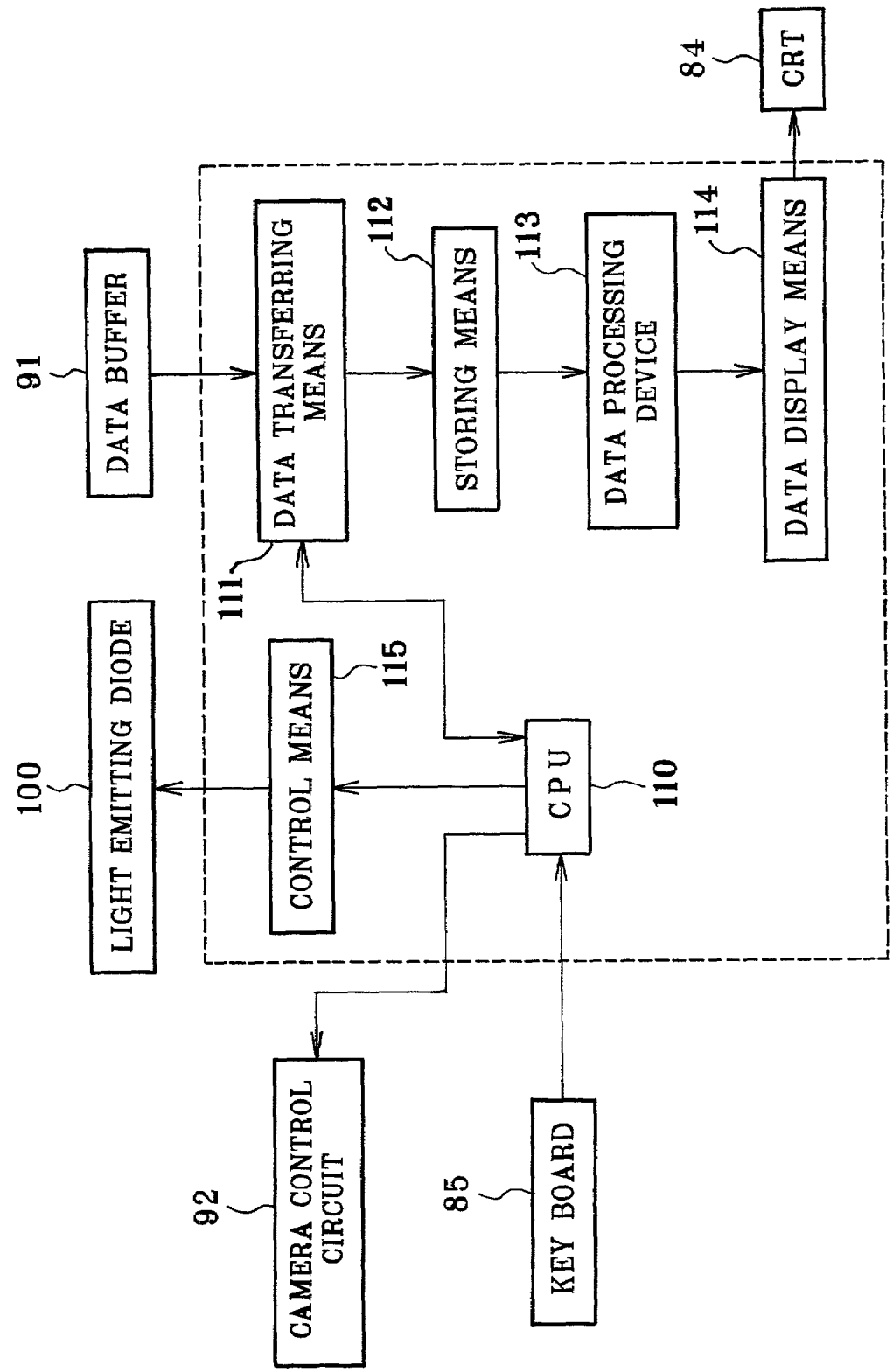
FIG. 19 is a block diagram of the data producing system.

As shown in FIG. 19, the personal computer 83 includes a CPU 110 for controlling the exposure of the cooled CCD camera 81, a data transferring means 111, a storing means 112, a data processing device 113, and a data display means 114. The data transferring means 111 reads the digital data from the data buffer 91, and the digital data is stored in the data storing means 112. Then the digital data is processed by the data processing device 113, and the data display means 114 displays a visual data on a screen of the CRT based on the processed digital data.

The light emitting diode 100 is controlled by a control means 115, in which an instruction is input from the keyboard 85 through the CPU 110. The CPU 110 outputs several signals to the camera controlling circuit 92 of the cooled CCD camera 81.

When the chemiluminescent data are read out, the filter 102 is removed. Then, while the light emitting diode 100 is kept off, the biochemical analysis unit 1 is placed on the diffusion plate 103 in the situation that the labeling substances in the absorptive regions 4 contacts the chemiluminescent substances.

Then, the focusing of the camera lens 97 is carried out by an operator, and the black box 82 is closed. Thereafter, the operator inputs an exposure starting signal from the keyboard 85 through the CPU 110 into the camera controlling circuit 92 of the cooled CCD camera 81. The camera control circuit 92 drives to open the shutter 89 and the CCD 86 to carry out the exposure.

The chemiluminescent emission emitted from the biochemical analysis unit 1 reaches a surface of the cooled CCD 81 in the cooled CCD camera 81 to form an image on the surface. The cooled CCD camera 81 receives thus the chemiluminescent emission and accumulates an analog data thereof in form of electric charges therein.

Note that in order to receive chemifluorescent emission, the chemiluminescent substrates may be recorded on the absorptive regions 4. After contacting to the chemiluminescent substrates, the labeling substances emit the chemiluminescence, and the chemiluminescence is received. In this case, the data generating system may have none of the light emitting diode 100, the filters 101, 102, and the diffusion plate 103.

As the base plate 5 is pressed to the absorptive material 2 in the biochemical analysis unit 1, the chemiluminescent emission emitted from the absorptive region 4 does not mixed with that from the neighboring absorptive region 4.

When a predetermined time has passed for the exposure, the CPU 110 outputs an exposure completion signal to the camera control circuit 92 of the cooled CCD camera 81. When the camera control circuit 92 receives the exposure completion signal from the CPU 110, the analog data is transmitted to the A/D converter 90 and transformed into a digital data. The digital data is stored in the data storing means 112.

When the operator inputs an instruction signal through the keyboard 85 in the CPU 110, the CPU 110 controls the data storing means 112 to send the digital data in the data processing device 113. The data processing device 113 processes the digital data. Thereafter, the CPU 110 sends the instruction signal to the data display means 114, and the chemiluminescent data is indicated on the CRT 84 based on the digital data.

When the fluorescent data are read out, the biochemical analysis unit 1 is placed on the diffusion plate. Then, the focusing of the camera lens 97 is carried out by an operator, and the black box 82 is closed. Thereafter, the operator inputs an exposure starting signal from the keyboard 85 through the CPU 110 into the camera controlling circuit 92 of the cooled CCD camera 81. The camera control circuit 92 drives the shutter 89 to open and the CCD 86 to perform the exposure.

The fluorescence emitted from the biochemical analysis unit 1 reaches a surface of the CCD 86 in the cooled CCD camera 81 to form an image on the surface. The CCD 86 receives thus the fluorescence and accumulates an analog data thereof in form of electric charges therein.

As the base plate 5 is pressed to the absorptive material 2 in the biochemical analysis unit 1, the fluorescence emitted from the absorptive region 4 does not mixed with that from the neighboring absorptive regions 4.

When a predetermined time has passed for the exposure, the CPU 110 outputs an exposure completion signal to the camera control circuit 92 of the cooled CCD camera 81. When the camera control circuit 92 receives the exposure completion signal from the CPU 110, the analog data is transmitted to the A/D converter 90 and transformed into a digital data. The digital data is stored in the data storing means 112.

When the operator inputs an instruction signal through the keyboard 85 in the CPU 110, the CPU 110 controls the data storing means 112 to send the digital data in the data processing device 113. The data processing device 113 processes the digital data. Thereafter, the CPU 110 sends the instruction signal to the data display means 114, and the fluorescent data is indicated on the CRT 84 based on the digital data.

In the embodiment, the absorptive material 2 is covered with the base plate 5, and the supporter 11 of the stimulable phosphor sheet 10 is formed of stainless which hardly transmits the radioactive ray. Accordingly, the electric beams emitted from the radioactive labeling substances are not scattered, and even if the absorptive regions 4 are formed in high density, the noise does not generate.

Further, the base plate 5 prevents the mixture of the fluorescence or the chemiluminescence emitted from the two or more absorptive regions 4.

In the embodiments the extremely small holes of the absorptive material 2 are disappeared by pressing onto the base plate 5, the specific binding material is absorbed only in the absorptive regions 4.

Further, by pressing of the absorptive material 2, it is neither stretched nor shrunken even after processing of hybridization. Accordingly, the stimulable phosphor sheet 10 is laid on the biochemical analysis unit 1 such that each stimulable phosphor layer region 12 may confront to each absorptive region 4.

Therefore, the biochemical analysis is more quantitatively carried out.

Other preferred embodiments will be now described.

Figure 20:
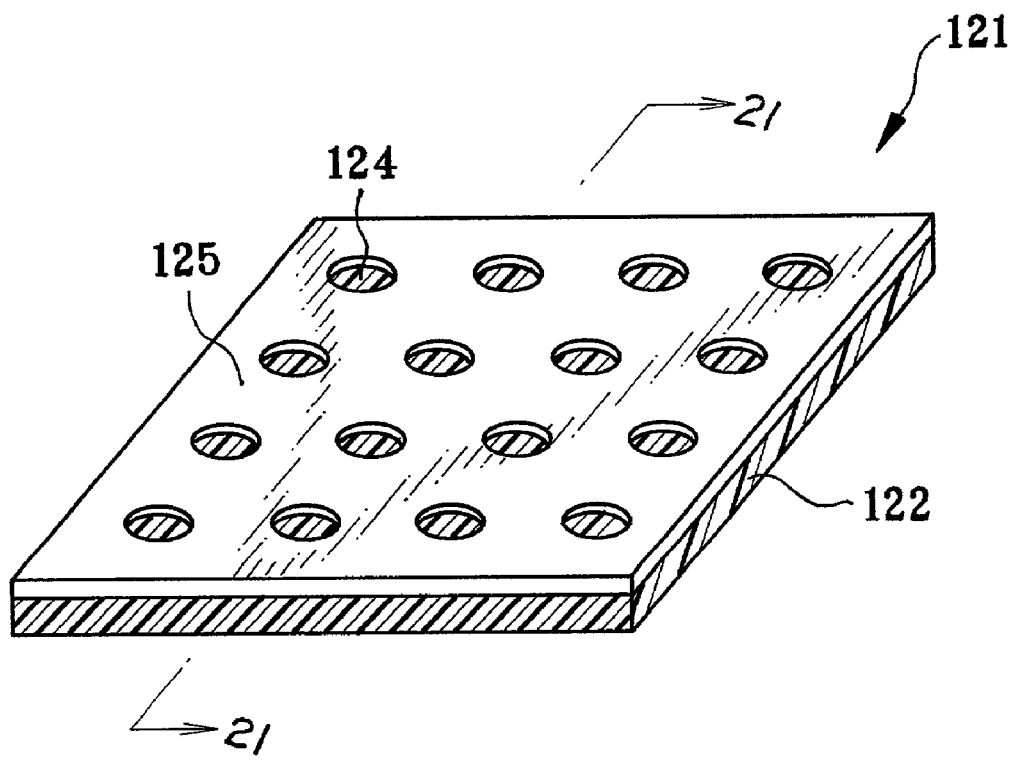
FIG. 20 is a perspective view of a biochemical analysis unit of the second embodiment of the present invention.
Figure 21:
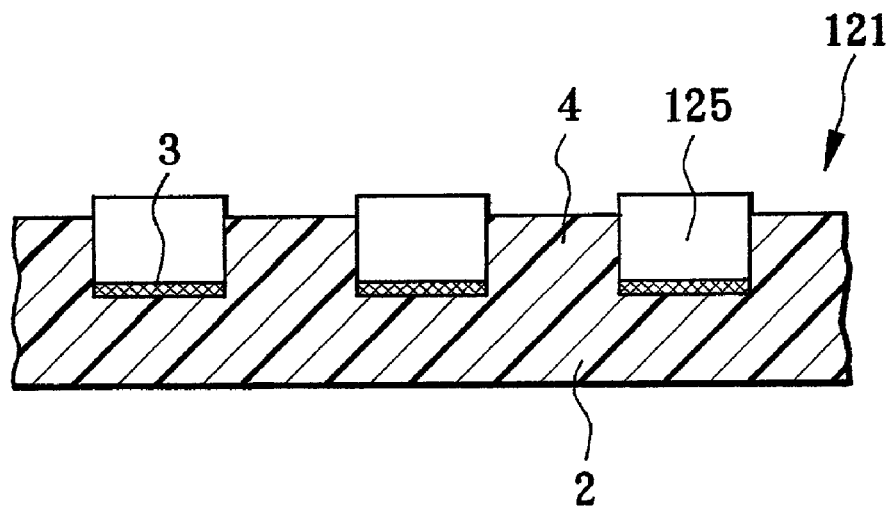
FIG. 21 is a cross-sectional view taken along a line 21—21 in FIG. 20.

In FIG. 20, a biochemical analysis unit 121 includes a base plate 125 formed of plastics. In FIG. 21, absorptive regions 124 are fitted in through-holes of the base plate 125, and a top of the absorptive region 4 is lower than a top of the base plate 125. The density of the absorptive regions 124 is as same as that of the absorptive regions 4.

Figure 22:
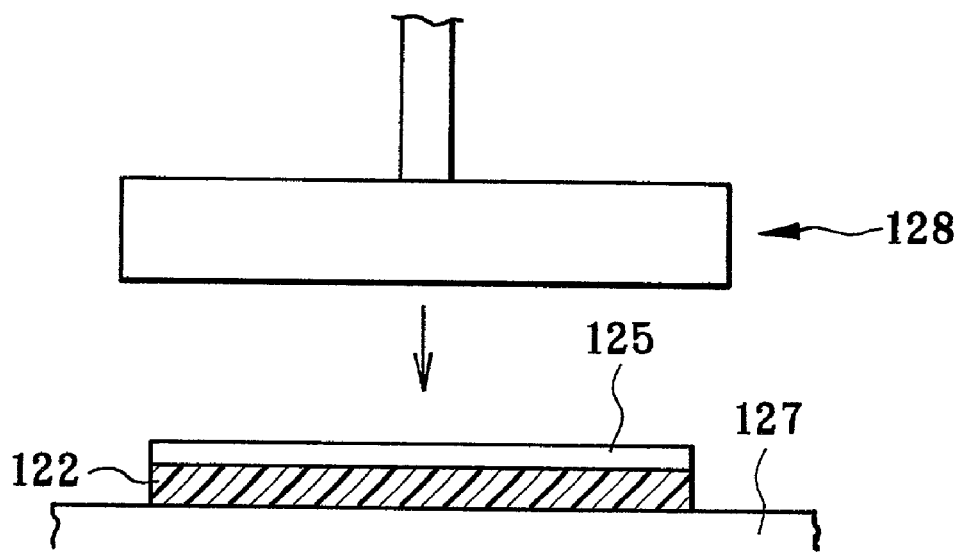
FIG. 22 is a front view illustrating a positional relation of the press plate to the biochemical analysis unit.

In FIG. 22, the biochemical analysis unit 121 is produced with a thermal pressing device including in a stage 127 and a press plate 128 whose temperature is adjusted.

The absorptive material 122 is set on the stage 127, and the base plate 125 is laid on the absorptive material 122. Then the plastic plate 5 is pressed by the press plate 128 while the absorptive regions 124 on the absorptive material 122 are fitted into the through-holes of the base plate 125. Note that the base plate 125, as formed of plastics, decreases the radioactive ray.

In the biochemical analysis unit 121, an area between the neighboring absorptive regions 4 on the absorptive material 2 is entirely covered with the base plate 125. Accordingly, the specific binding material on the absorptive region 4 does not flow onto the area of the absorptive material. Further, as the extremely small holes of the absorptive material 2 are disappeared by pressing onto the base plate 125, the specific binding material is absorbed only in the absorptive regions 124.

Figure 23:
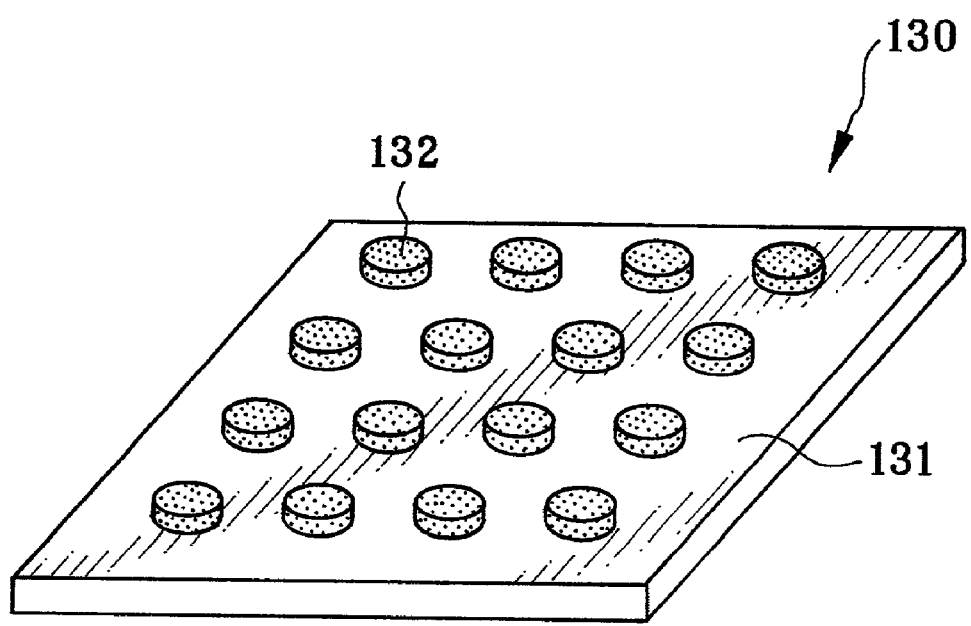
FIG. 23 is a perspective view of a stimulable phosphor sheet.

In FIG. 23, a stimulable phosphor sheet 130 includes a supporter 131 formed of stainless so as to shield the radioactive ray. The stimulable phosphor sheet 130. On a surface of the supporter 131 are formed a nearly circular stimulable phosphor layer regions 132 in the same pattern as that of the absorptive region 124 on the biochemical analysis unit 121 so as to protrude from the supporter 131.

Figure 24:
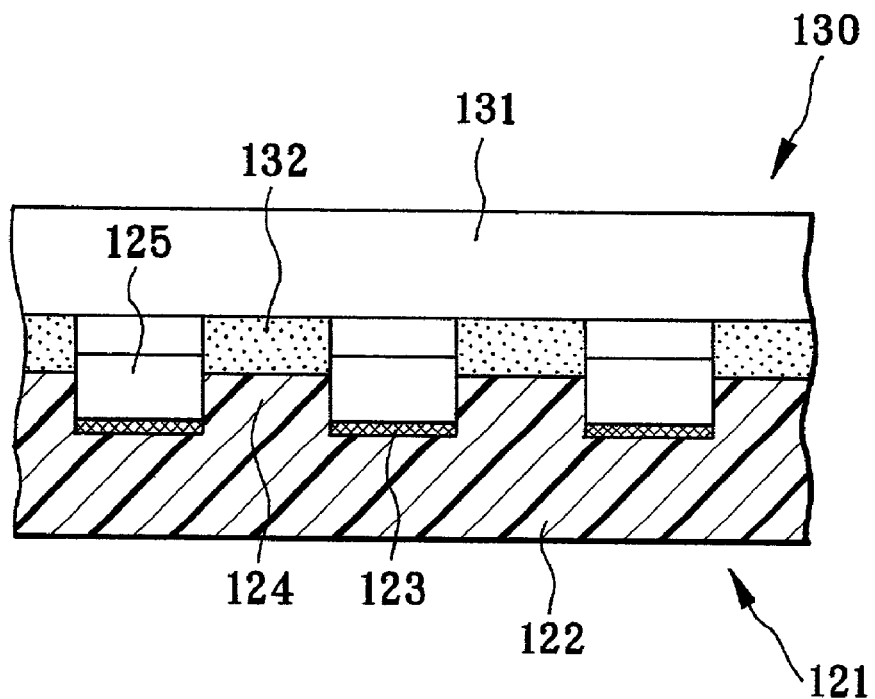
FIG. 24 is a cross-sectional view illustrating a situation when the stimulable phosphor sheet in FIG. 23 is superposed on the biochemical analysis unit in FIG. 22.

As shown in FIG. 24, when the exposure is carried out, the stimulable phosphor layer sheet 130 is laid on the biochemical analysis unit 121 such that the stimulable phosphor layer region 132 may confront to the absorptive region 124.

In the embodiment, as the base plate 125 is pressed on the absorptive material 122, the biochemical analysis unit 121 is neither stretched nor shrunken by processing in a solution such as hybridization. Therefore, each absorptive regions 124 confronts to the stimulable phosphor layer regions 132 when the stimulable phosphor sheet 130 is superposed on the biochemical analysis unit 121.

Figure 25:
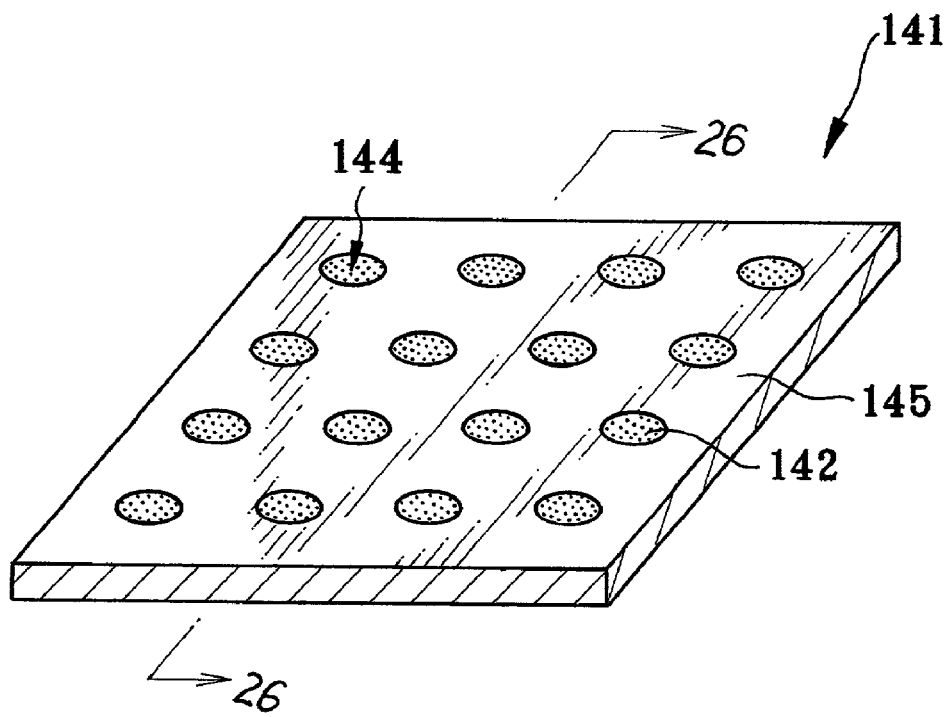
FIG. 25 is a perspective view of a biochemical analysis unit of the third embodiment of the present invention.

In FIG. 25, a biochemical analysis unit 141 includes an absorptive material 142 having absorptive regions 144 and a shielding region 145 formed around the absorptive regions 144. The shielding region 145 contains metallic colloids so as to shield the radioactive ray, the fluorescence and the chemiluminescence.

Figure 26:
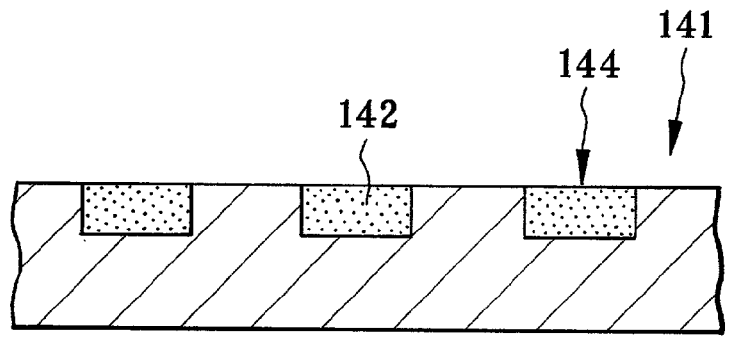
FIG. 26 is a cross-sectional view taken along a line 26—26 in FIG. 25.

As shown in FIG. 26, the absorptive regions 144 and the shielding region 145 construct a flat surface of the biochemical analysis unit 141. In order to form the absorptive regions 144, a surface of the absorptive material 142 is partly masked in the same pattern as that of the absorptive regions 144. Another part of the absorptive material 142 is applied with a disperse solution including the metallic colloids. Note that the number of the absorptive regions 144 is about 10000 and each of them has a size of about 0.01 mm². A density thereof is 5000 per cm².

In the embodiments the absorptive materials 2, 122, 142 of the respective biochemical analysis units 1, 121, 141 may be formed of not only the nylon-6, but also carbonated porous material, for example activated carbon, and other porous materials each of which has the extremely small holes and can be used for the membrane filter. As the porous materials there are, for example, aliphatic polyamide (nylon-6,6, nylon-4,10); cellulose derivatives (nitrocellulose, acetyl cellulose, cellulose acetate butyrate); collagen; alginic acid derivatives (alginic acid, calcium alginate, alginic acid/polylisinepolyion complex); polyolefins (polyethylene, polypropylene); polychlorovinyl; polychlorovinylidene; polyfluorovinylidene; polytetrafluoride, and their copolymers or complexes. Further, the absorptive materials 2, 122, 142 may be formed of inorganic porous materials, such as metals (platinum, gold, iron, silver, nickel, aluminum); oxides of metals (alumina, silica gel, titania, zeolite); salts of metals and their complexes (hydroxiapatite, calcium sulfate); and plural fibers.

The base plates 5 and 125 may be attached with other appropriate method than the pressing and the thermal pressing.

The base plates 5 and 125 may be formed of a material which decreases the radioactive ray and the light and has a plurality of through-holes. Further, the supporter of the stimulable phosphor sheet may be also formed of the material which decreases the radioactive ray. As the material used for the base plate and the supporter, there are metals (for example, gold, silver, cupper, zinc, aluminum, titanium, tantalum, chromium, iron, nickel, cobalt, lead, tin, selenium and the like); alloys (for example, brass, stainless, bronze and the like); silicone materials (silicone, amorphous silicone, glass, quartz, silicone carbide, silicone nitrate and the like); oxides of metals (aluminum oxide, magnesium oxide, zirconium oxide and the like); inorganic salts (tungsten carbide, calcium carbonate, calcium sulfate, hydroxiapatite, gallium arsenide, and the like). These may have a structure of single crystal, amorphous, or sintered polycrystal. As the organic materials, high molecular compounds are preferably used, for example, polyolefin (polyethylene, polypropyrene and the like); acryl resins (polymethyl methacrylate, butylacrylate/methylmethacrylate copolymer and the like); polyacrylonitrile; polyvinylchrolide; polyvinylidenechrolide; polyvinylidenefluoride; polytetrafluoroethylene; polychlorotrifluoroethylene; polycarbonate; polyesters (polyethylene naphthalate, polyethylene terephthalete and the like); aliphatic polyamides (nylon-6, nylon-6,6, nylon-4,10 and the like); polyimide; polysulfone; (polyphenylene sulfide); silicon resins (polydiphenylsiloxane and the like); phenol resins (novolac and the like); epoxy resins; polyurethane; polystyrene; butadiene-styrene copolymer; polusaccharides (cellulose, acetyl cellulose, nitrocellulose, starch, calcium alginate, hydroxypropyl methyl cellulose and the like); chitin; chitosan; urushi (Japanese lacquer); polyamide (gelatin, collagen, keratin and the like), copolymers of these high molecular materials. These may be complex materials. In the complex materials particles of oxides of metals or glass fiber may be added, or the organic compound may be blended if necessary.

Note that in the biochemical analysis units 1, 121 it is not necessary to apply the adhesive agents 3, 123. Further, when only the radioactive data is read, there may be formed around the absorptive regions 4, 124, 144 a region through which the radioactive ray transmits and the chemiluminescence and the fluorescence do not. When only the chemiluminescent data and the fluorescent data are read, there may be formed around the absorptive retions 4, 124, 144 a region through which the chemiluminescence and the fluorescence transmit and the radioactive ray does not.

The absorptive regions 4, 124, 144 may have other shapes such as rectangularly-formed shape. The size thereof may be optionally decided, and preferably ten or more thereof is arranged in 5 mm². The density thereof may be 10/cm² or more. Further, the absorptive regions 4, 124, 144 may be not formed regularly.

Each of the stimulable phosphor layer regions 12, 132 may have a size more than the absorptive regions 4, 124. Further, the stimulable phosphor layer regions 12, 132 may have other shapes such as rectangularly-formed shape. They may be not formed regularly when in same pattern as that of the absorptive regions 4, 124.

The stimulable phosphor is preferably exited by a visible rays as follows: for example, Japanese Patent Laid-Open Publication No. S55-12145 discloses alkaline earth material fluoride halide phosphors $(Ba_{1-x}M_{2+x})FX:yA$ (herein $M^{2+}$ is at least one of alkaline earth material Mg, Ca, Sr, Zn and Cd, X is at least one halogen of Cl, Br and I, and A is Eu, Tb, Ce, Tm, Dy, Pr, He, Nd, Yb and Er; $0 \leq x \leq 0.6$, $0 \leq y \leq 0.2$. Japanese Patent Laid-Open Publication No. H2-276997 discloses alkaline earth material fluoride halide phosphors SrFX:Z (herein X is halogen, at least one of Cl, Br and I, and Z is Eu or Ce). Japanese Patent Laid-Open Publication No. S59-56479 discloses europium activated complex halogen phosphors $BaFX.xNaX':aEu^{2+}$ (herein each X and X' is halogen, at least one of Cl, Br and I; $0<x \leq 2$, $0<a \leq 0.2$). Japanese Patent Laid-Open Publication No. 58-69281 discloses cerium activated metal Oxyhalide, MOX:xCe (herein M is at least one of metals, Pr, Nd, Pm, Sm, Eu, Tb, Dy, Ho, Er, Tm, Yb and Bi, X is halogen, one or both of Br and I; $0<x<0.1$). Japanese Laid-Open Publications No. 60-101179 and 60-90288 disclose cerium activated rear earth material oxyhalide phosphors LnOX:xCe (herein Ln is at least one of rear earth elements Y, La, Gd and Lu, X is at least one of halogens Cl, Br and I; $0<x \leq 0.1$). Japanese Patent Laid-Open Publication No. S59-75200 discloses europium activated complex halide phosphor, $M^{(2)}FX.aM^{(1)}X'.bM'^{(2)}X''_2.cM^{(3)}X'''_3.xA:yEu^{2+}$ (herein $M^{(2)}$ is at least one of alkaline earth materials Li, Na, K, Rb and Cs, $M'^{(2)}$ is at least one of Be and Mg, $M^{(3)}$ is at least one of Al, Ga, In and Tl, A is at least one of oxides of metal, X is at least one of halogens Cl, Br and I, each X', X'' and X''' is one of halogens F, Cl, Br and I; $0 \leq a \leq 2$, $0 \leq b \leq 10^{-2}$, $0 \leq c \leq 10^{-2}$, $a+b+c \geq 10^{-2}$, $0<x \leq 0.5$, and $0<y \leq 0.2$).

There are further other embodiments of the present invention, which will be described now.

Figure 27:
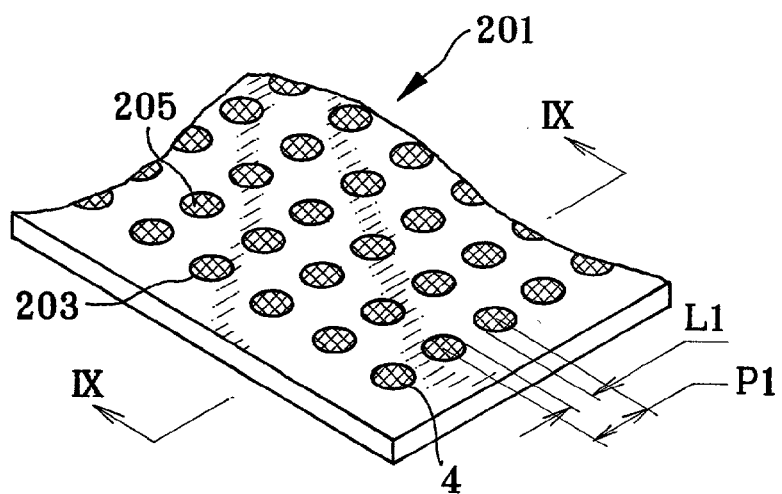
FIG. 27 is a perspective view of a biochemical analysis unit of the forth embodiment of the present invention.

As shown in FIG. 27, a biochemical analysis unit 201 includes a base plate 205 in which through-holes 206 are formed. The through-hole 206 is provided with an absorptive region 204 which is formed of the porous materials used for producing the absorptive region 4. On the absorptive region 204, specific binding materials are dropped.

The base plate 205 has a thickness between 50–1000 μm, preferably 100–500 μm, and is formed of the same materials for the base plates 5 and 125. Accordingly, the intensity of the radioactive ray, the fluorescence and the chemiluminescence each preferably becomes under 1/5, especially under 1/10.

The density of the base plate 205 is more than 0.6 g/cm$^3$, preferably 1–20 g/cm$^3$, especially more than 2–10 g/cm$^3$. If the radioactive labeling substances, such as $^{32}$P, $^{33}$P, $^{35}$S, $^{14}$C and the like are applied on the absorptive region 204, the base plate 205 of the above density can effectively shield the radioactive ray such that the noise may not generate in the biochemical analysis data.

Further, according to the number, the density and the pattern, the absorptive region 204 are formed as same as the absorptive region 4. Usually, a length or hole pitch P1 between centers of the nearest absorptive regions 204 is 0.05–3 mm, and a distance L1 between the nearest absorptive regions 204 is 0.01–1.5 mm.

Figure 28:
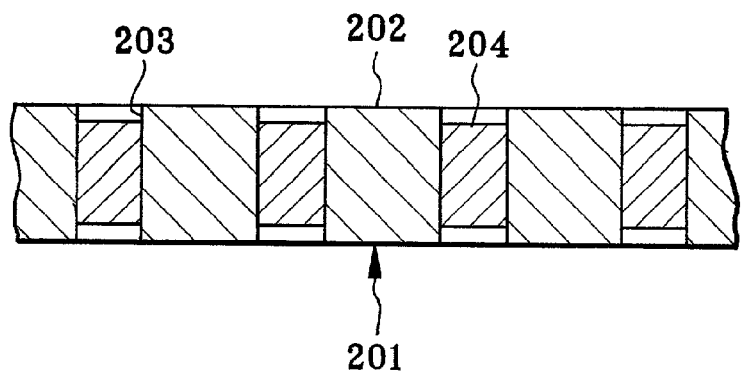
FIG. 28 is a cross-sectional view taken along a line IX—IX in FIG. 27.

As shown in FIG. 28, the absorptive regions 204 are preferably retracted from the surface of the base plate 205. In this structure, the specific binding substances can be more easily absorbed in each of the absorptive regions 204, and the specific binding substances hardly flow out to the other absorptive regions 204.

Further, the through-holes 206 may be formed by a method of an electrical discharging. In the method, a discharging member is used and has electrodes arranged in the same pattern as the through-holes 6. The discharging member is closed to the base plate, and thereafter biases a high voltage between the electrodes in a pulse-like manner. Thereby the base plate is heated such that parts thereof are volatilized.

Figure 29:
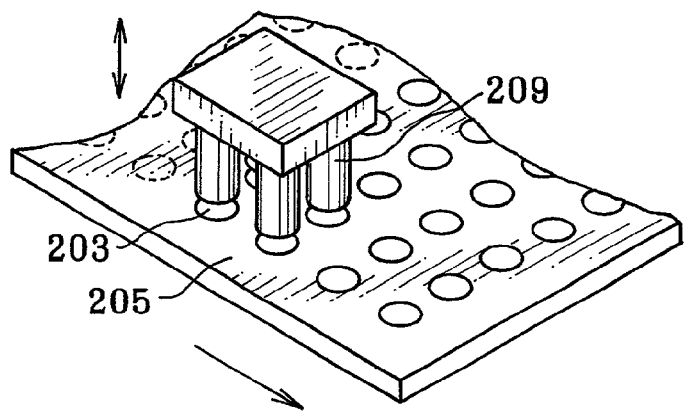
FIG. 29 is perspective view illustrating a situation when through-holes are formed by a punch.
Figure 30:
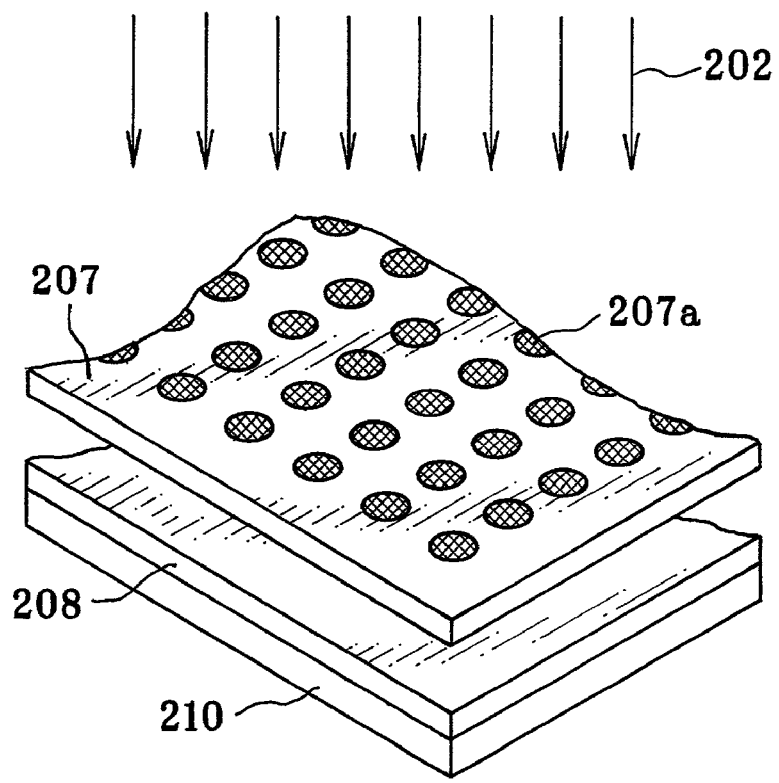
FIG. 30 is perspective view illustrating a situation when the through-holes are formed by photo lithography and etching.
Figure 31:
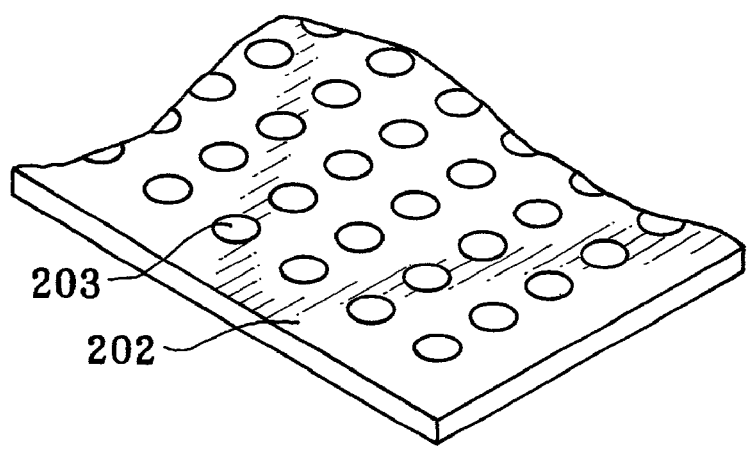
FIG. 31 is a perspective view of a base plate used for the biochemical analysis unit of the forth embodiment.

As shown in FIG. 29, the through-holes 206 may be formed by using a punch 209. Further, as shown in FIG. 30, the though-holes 206 may be formed by photo lithography and etching. In this case, a supporter 210 is coated with a coating layer 208 which is formed of a photosensitive material. Then, a mask sheet 207 for photolithograph is laid on the coating layer 208. The mask sheet 207 has light-shielding regions 207a arranged in a pattern of the through-holes 206 to be formed in the base plate 205. An ultraviolet ray 202 is applied through the mask-sheet 207 to the coating layer 208. However, as the light shielding regions 207a shield the light, the coating layer 208 is solidified without parts corresponding to the light-shielding regions 207a. Thereafter, etching is carried out. Namely, the coating layer 208 is dipped in an organic solution to remove the parts thereof that are not solidified, peeled from the supporter 210, and formed into the base plate 205 in FIG. 31. Note that the supporter 210 may be formed of polyethylene, polypropyrene, polyethylene terephthalate, polytetrafluoroethylene and the like. However, the present invention is not restricted in them.

As the photosensitive materials, ultraviolet curting compounds are preferably used. The ultraviolet curting compounds are composed of photo polymerization initiator and ultraviolet curting resins. There are several types of the photo polymerization initiator, such as hydrogen-pull initiator (for example, benzophenone type stabilizer), and radical cleavage type stabilizer (for example, acetophenone type stabilizer and triazine type stabilizer). Further, as the ultraviolet curting resins, there are acrylic acid ester (for example, acrylic acid ethyl, acrylic acid butyl, acrylic acid-2-ethylhexyl), methacrylic acid ester (methacrylic acid methyl, methacrylic acid ethyl, methacrylic acid butyl, ethylenegrycol dimethacrylate), higher alcohol, (metha-) acrylic acid ester (for example, ethylene grycole dimethacrylate, 1,4-dicycrohexane diacrylate, pentaerythritol tetra(metha)acrylate, pentaerythritol tri(metha)acrylate, trimethylol propanetri(metha)acrylate, trimethylol ethane tri(metha)acrylate, dipentaerythritol tetra(metha)acrylate, dipentaerythritol penta(metha)acrylate, penta erythritol hexa (metha)acrylate, 1,2,3-cycrohexane tetramethacrylate, polyurethane polyacrylate, polyester polyacrylate). However, present invention is not restricted in them. Further, they may be used separately or mixed.

As the organic solvents for the etching, ketones such as acetone and ethylmethylketone are used. The organic solvent may solve the ultraviolet cursing materials and is not restrict in them. Further, the etching is preferably carried in ultrasonic wave.

In order to form the through-holes 206 in the base plate 205, high power laser beams emitted from exima laser, the YAG laser and the like may be also applied to the base plate 205. Thereby parts of the base plate 205 may be are evaporated. Furthermore, electrodes arranged in the same pattern of the through-holes 206 may be also set to the base plate 205 in nonconductors such as oils or air. The electrodes are electrically biased in high voltage. Thus, there may occur s discharge between them to form through-holes 206.

When the base plate 205 is formed of metal, the through-holes 206 are etched on the base plate 205. A resist sheet having the same pattern of the through-holes 206 is laid on a metal plate. The metal plate is set to a light. Thereafter, the metal plate is disposed in solutions of strong acid such as sulfuric acid, fluoric acid, phosphoric acid. In the solutions an anode of the platinum plate and a cathode of metallic plate are provided to carry out etching. Thereby corresponding to the pattern of the resist sheet, the through-holes 206 are formed in the metal plate. Then, the resist sheet is removed to obtain the base plate 205.

In order to form the absorptive region 204 in the through-hole 206, there are at least two methods.

Figure 32:
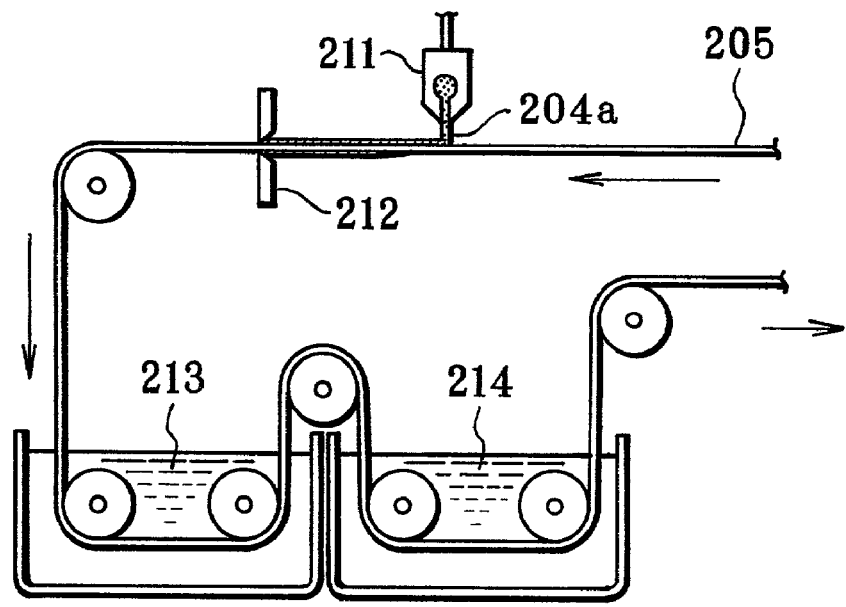
FIG. 32 is a diagrammatic view illustrating a situation when absorptive regions are formed in the through-holes by using a dye.

First, as shown in FIG. 32, the base plate 205 is fed in an arrowed direction, and a dye 211 containing a dope 204a is disposed upwards from the base plate 205. The dye 211 feeds out the dope 204a over the base plate 205. A part of the dope 204a enters in the through-hole 206, and an excess of the dope 204a that remains on the base plate 205 is removed by a blade 212. Thereafter, the base plate 205 is set in a solidizing liquid 13 composed of at least one of good solution and bad solution of the porous materials. Thus the absorptive regions 204 are formed and the base plate 205 is cleaned in a water 14 and dried.

A density of the dope 4 is usually 5–35 wt. %, preferably 10–30 wt. %. If the density is less than 5 wt. %, a structure of the porous materials forming the absorptive regions 204 is not enough strong. If the density is more than 35 wt. %, porous spaces becomes smaller, which decreases the chemical affinity of the porous material to the substances derived from the living organism.

Figure 33:
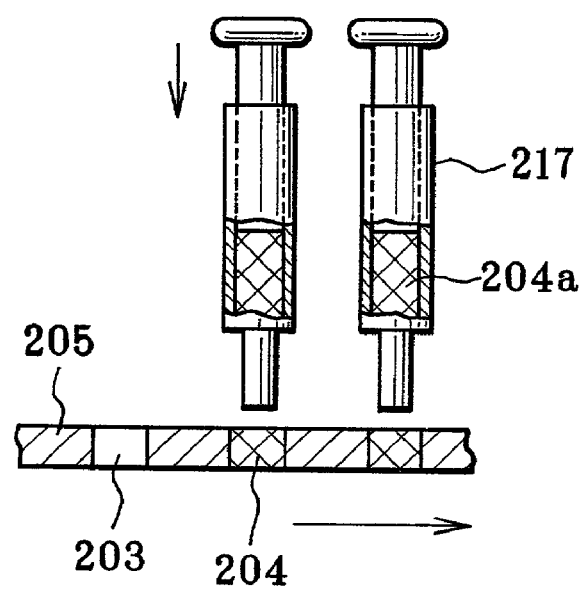
FIG. 33 is an exploded schematic view illustrating a situation when the absorptive regions are formed in the through-holes by using dispensers.

In FIG. 33, the base plate 205 is fed in an arrowed direction. Above the base plate 205, dispensers 217 provide the dope 204a in the through-holes 206. After providing the dope 204a, an air of regulated temperature and humidity is blown to the base plate 205 to volatile the solvents. Thus the dope 204a is separated into several layers and gelated.

In order to remove the excess of the dope 204a, suctioning devices (not shown) are provided up- and downward of the base plate 205.

In order that the specific binding substances are more effectively absorbed, the porous material may contain surface-active agent. As the surface-active agents, there are cation, fluoride types: for example, dodecylbenzenesulfonic potassium, saponin, p-tert-octylphenoxyethoxyethylsulfonic potassium, nonylphenoxy-polyethoxy-ethanol; fluoride type surface-active agents which are disclosed in Japanese Patent Laid-Open Publications No. S62-170950, S63-188135 and U.S. Pat. No. 5,380,644; and polyalkyreneoxide and anion type surface-active agents which are disclosed in Japanese Laid-Open publication No. H6-301140.

According to the porous material in the absorptive regions 204, an angle of contact to water is preferably less than 60°, especially less than 50°.

The porous materials may be adhered to the base plate 205 with an adhesive agent such as epoxy. There is also another preferable method, for example, oxides of metals had to be provided on a surface of the base plate 205.

Figure 34A:
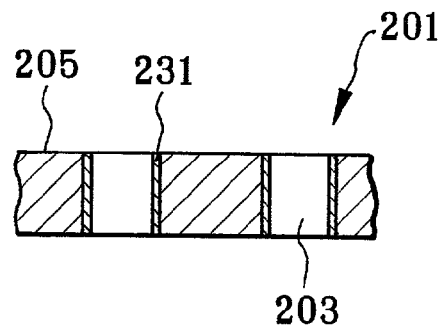
FIG. 34A is a sectional view of the base plate illustrating a situation when a layer of oxide of metal is formed.
Figure 34B:
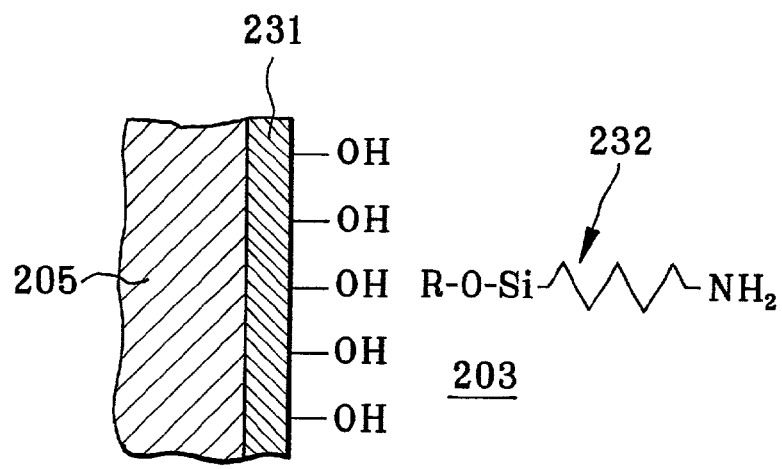
FIG. 34B is an exploded view of FIG. 33A, illustrating a situation of a coupling agent in the through-hole.
Figure 34C:
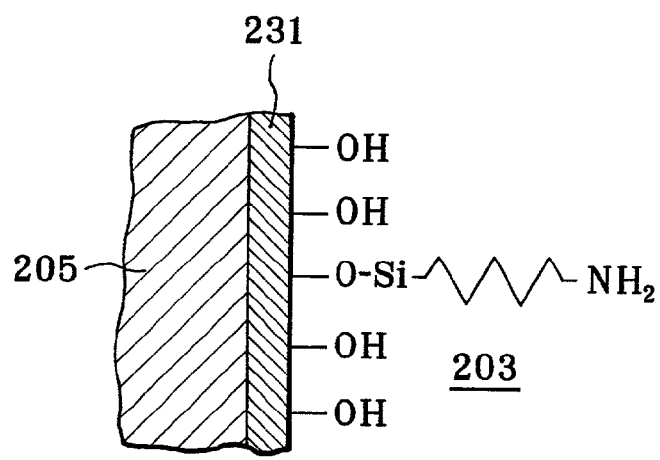
FIG. 34C is a same view of FIG. 33B, illustrating a situation when coupling agent is bound to the layer of oxide of metal.

When the base plate 205 is formed of metal, the oxides of the metals are produced on the surface of the base plate 205 by a cathode oxidizing process. In the cathode oxidizing process, the base plate 205 is disposed as a cathode in a solution of sulfuric acid, phosphoric acid and chromic acid. Then the straight flow is applied through the base plate 205. Thereafter, as shown in FIG. 34A, a layer 231 of the oxides of metals is formed on a wall surrounding the through-hole 206. Then the base plate 205 is set in a coupling agent 232 of silane type or titanate type having an alcoxyde in an end and an amino group or a carboxylic group in another end. Thus, as shown in FIG. 34B, the coupling agent 232 is provided in the through-hole 206. While the base plate 205 and the coupling agent 232 is heated in a temperature above 50° C., as shown in FIG. 34C, a hydroxide group on the surface of the layer 231 combines with the coupling agent 232.

Figure 35A:
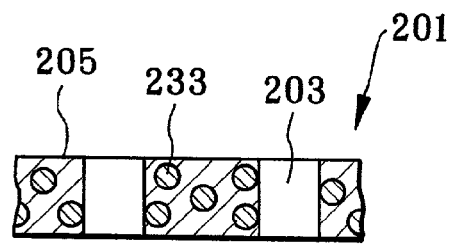
FIG. 35A is a sectional view of the base plate formed of plastic.
Figure 35B:
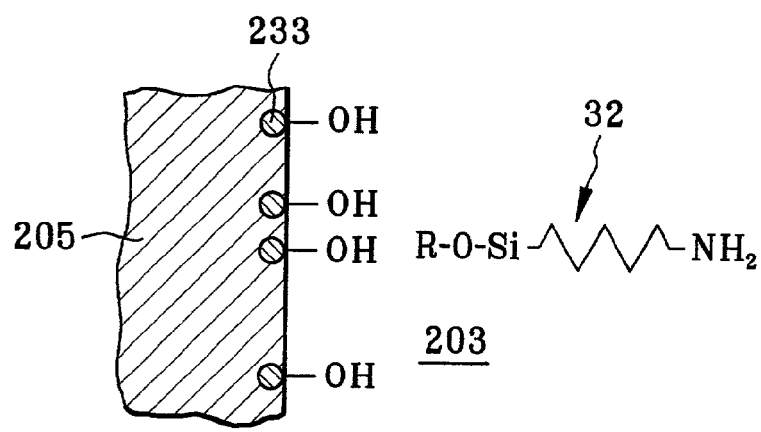
FIG. 35B is an exploded view of FIG. 33A, illustrating a situation of a coupling agent in the through-hole.
Figure 35C:
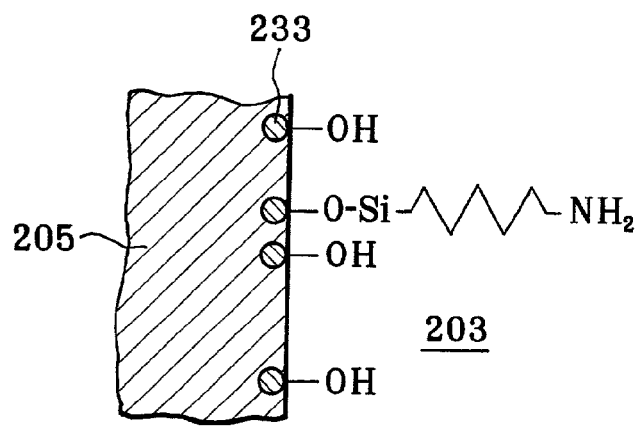
FIG. 35C is a same view of FIG. 34B, illustrating a situation when coupling agent is bound to the layer of oxide of metal.

When the base plate 205 is made of plastics, as shown in FIG. 35A, particles 233 of the oxides of metals are diffused in the base plate 205. As shown in FIG. 35B, the particle 233 on the surface of the base plate 205 has a hydroxide group. While the base plate 205 and the coupling agent 232 are heated in a temperature above 50° C., as shown in FIG. 35C, the hydroxide group on the particle 233 combines with the coupling agent 232.

After combining of the hydroxide group with the coupling agent 232, the porous material is combined with another end of the coupling agent 232. Thus the porous material is adhered to the base plate 205. Note that the coupling agent 232 may be sprayed for providing in the base plate 205.

Figure 36:
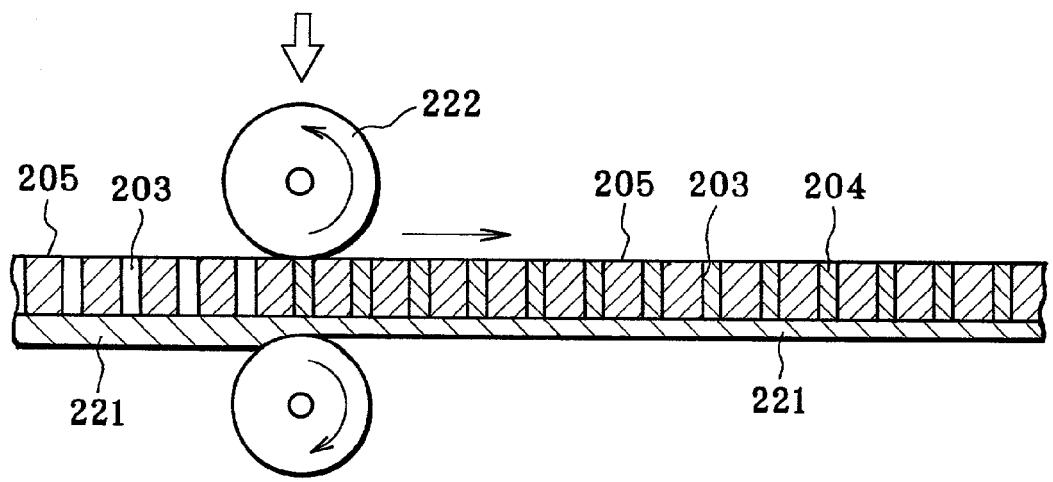
FIG. 36 is a sectional view illustrating a situation in which the biochemical analysis unit of the forth embodiment is formed by using a press roller and a back-up roller.

In FIG. 36, a porous material layer 221 formed of the porous material is provided on the base plate 205, and a pair of a press roller 222 and a back-up roller 223 nips the base plate 205 to pressing the porous material of the porous material layer 221 into the through-hole 206. Thereby the press roller 222 and the back-up roller 223 may be heated such that the porous material layer 221 may be softened. After pressing the porous material into the through-hole 206, the absorptive regions 204 are formed.

In order to provide the porous material layer 221, a dope is applied on a supporter (not shown). Then, the supporter is laid in a bad solution, or in the mixture of the bad solution and good solution. Thereafter, the dope is dried by cleaning in water or by applying the dope on the supporter.

A density of the porous materials in the absorptive region 204 and the porous material layer 221 is usually less than 1.0 g/cm$^3$, preferably less than 0.5 g/cm$^3$, especially 0.1 g/cm$^3$, in order to effectively absorb the specific binding substances bound such as nucleic acid, fragments thereof, and synthetized oligonucleotide (synthetic oligonucleotide). The density of the porous material in the absorptive region 204 must be smaller that of the base plate.

The porous material in the absorptive material 204 has extremely small holes whose radius is 0.1–50 μm. The extremely small holes form free spaces of 10–90% therein.

Figure 37:
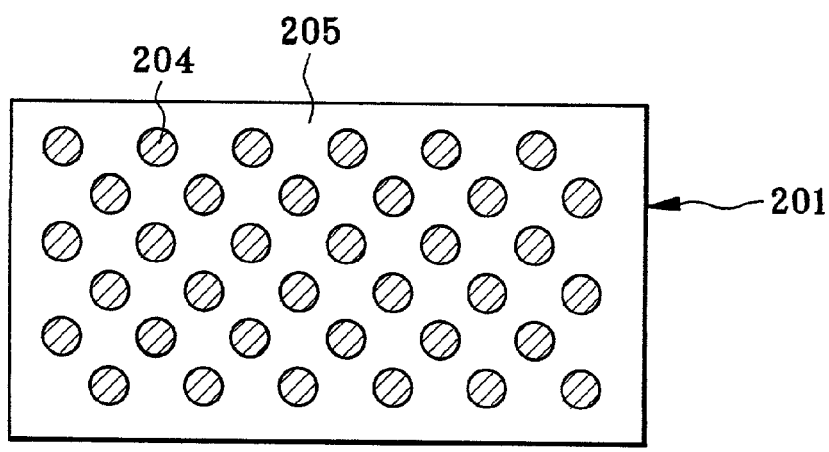
FIG. 37 is a plan view of the biochemical analysis unit of the forth embodiment, in which the absorptive regions are formed in another pattern.
Figure 38:
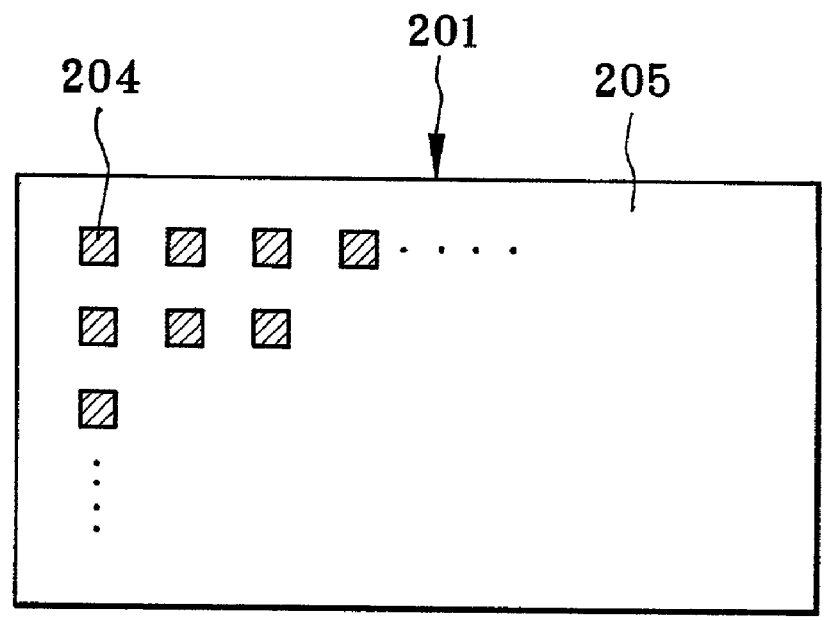
FIG. 38 is a plan view of the biochemical analysis unit of the forth embodiment, in which the absorptive regions are tetragonaly-shaped.
Figure 39:
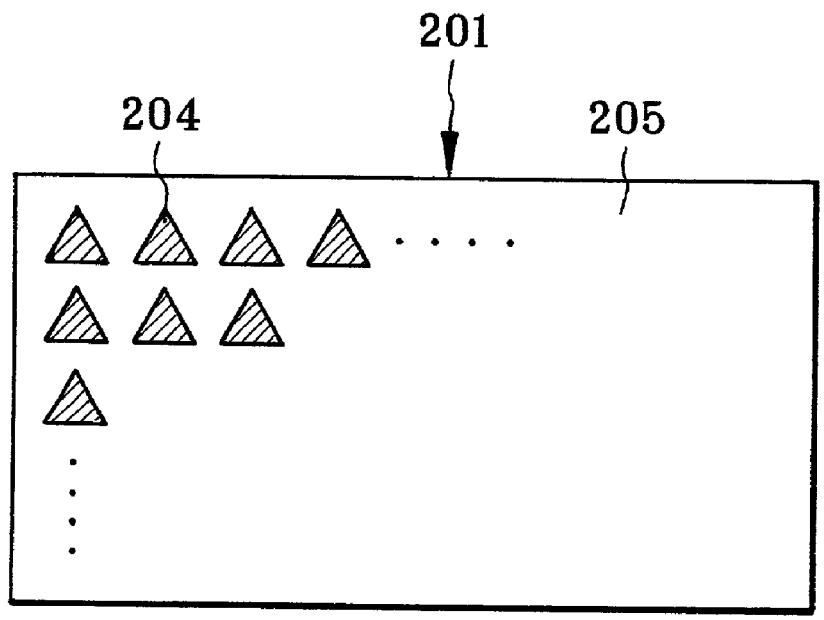
FIG. 39 is a plan view of the biochemical analysis unit of the forth embodiment, in which the absorptive regions are triangularly shaped.

In FIG. 37, the pattern of the absorptive regions 204 is arranged. Further, the absorptive regions 204 may be formed in other shapes such as hexangular, ellipse and the like. In FIG. 38, absorptive regions 204 are tetragonaly-formed, and in FIG. 39, absorptive regions 204 is triangularly-formed.

[Embodiment 1]

(1) Produce of a Base Plate Having Through-holes

A polyester sheet has a size 80mm×80mm and a width of 120 μm. A density of the polyesther sheet is 1.0 g/cm$^3$. Circular holes whose radius is 0.2 mm are formed in the polyesther sheet (base material sheet) with a hole pitch 0.3 mm, and a distance 0.1 mm. 10×10 holes construct a unit and 6400 holes are formed in the polyester sheet.

| (2) Supply for porous material | |
|---|---|
| Polysulfone (P-3500, UCC Corporations) | 15 part by weight |
| N-methyl-2-pyrrolidone | 72 part by weight |
| Polyvinyl-pyrrolidone | 13 part by weight |
| Water | 1.2 part by weight |

Above materials are solved to prepare a solution for supplying for the porous material. The solution is flown out on the polyesther sheet with a casting coaster, supplied in the through-hole. Thereafter, the excess of the solution is removed with a blade. The polyester sheet is set in an air blowing in 1.2 m/s at 25° C., and humidity of 50%. Then, the polyester sheet is set in a water of 25° C. to form the extremely small holes. Thereafter, the polyester sheet is set in diethylene glycol for five minutes, washed in water and dried. Thus the biochemical analysis unit 201 is obtained that is constructed of polyester dissepiment and porous polymer filled area. Herein an average of radius of the holes is 0.2 μm, and a dried layer is formed to be 120 μm in width.

[Embodiment 2]

(1) Produce of Base Plate Having Through-holes

A SUS 340 sheet has a size 80 mm×80 mm and a width of 100 μm. A density of the SUS 340 sheet is 1.0 g/cm$^3$. Circular holes whose radius is 0.2 mm are formed in the polyesther sheet with a hole pitch 0.3 mm, and a distance 0.1 mm. 10×10 holes construct a unit and 6400 holes are formed in the polyester sheet.

| (2) Supply for porous material | |
|---|---|
| Nylon-6 (Polysciences Corporation) | 14 part by weight |
| Formic acid | 66 part by weight |
| Water | 20 part by weight |

Above materials are solved to prepare a solution for forming porous structure. The solution is doped on the polyesther sheet with a casting coaster, supplied in the through-hole. Thereafter, the excess of the solution is removed with a blade. The SUS 340 sheet is set in 40% formic acid aqueous solution to form the extremely small holes. Thereafter, the SUS 340 sheet is washed in water and dried.

Thus the biochemical analysis unit is obtained that is constructed of polyester dissepiment and porous polymer filled area. Herein an average of radius of the holes is 0.5 μm, and a dried layer is formed to be 160 μm in width.

| (3) Prepare of porous structure | |
| --- | --- |
| Nylon-6 (Polysciences Corporation) | 14 part by weight |
| Formic acid | 66 part by weight |
| Water | 20 part by weight |

Above materials are solved to prepare a solution for supplying for the porous material. The solution is doped as the dope on the polyester sheet with a casting coaster, supplied in the through-hole. Thereafter, the excess of the solution is removed with a blade. The SUS 340 sheet is set in 40% formic acid aqueous solution to form the extremely small holes. Thereafter, the SUS 340 sheet is washed in water and dried. Thus the biochemical analysis unit is obtained that is constructed of polyester dissepiment and porous polymer area. Herein an average of radius of the holes is 0.5 μm, and a dried layer is formed to be 160 μm in width.

(4) Forming of Biochemical Analysis Unit

The base plate obtained in the process (1) that the porous material obtained in the process (3) is laid on is fed to a pair of a press roller and a back-up roller, and pressed in a pressure 20 kgf/cm² to obtain a biochemical analysis unit.

(5) Estimation of Biochemical Analysis Unit

A fragment of nucleic acid is supplied in porous material of each of the biochemical analysis units obtained in the embodiments 1 and 2. Thereafter, the biochemical analysis unit is set in an aqueous solution of radioactive labeling substances to carry out the hybridization. After withdrawing the biochemical analysis unit from the aqueous solution, it is washed in water and dried. A stimulable phosphor sheet is laid on the biochemical analysis unit and operation of radio autography is carried out in a room temperature. Then, a radioactive data can be read out from the stimulable phosphor sheet in high resolution and high sensitivity.

Figure 40:
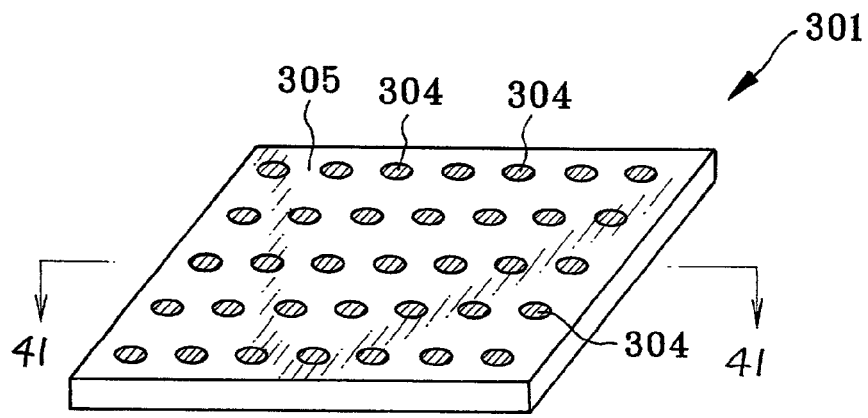
FIG. 40 is a perspective view of a biochemical analysis unit of the fifth embodiment.
Figure 41:
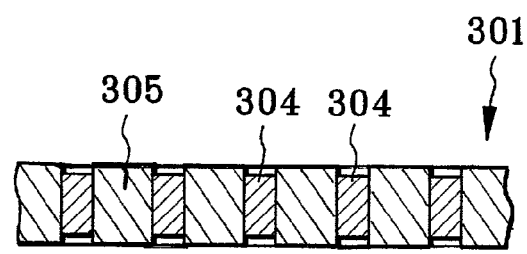
FIG. 41 is a cross-sectional view taken along a line 41—41 in FIG. 40.

In FIG. 40, a biochemical analysis unit 301 has a base plate 305 and an absorptive region 304. As shown in FIG. 41, the absorptive region 304 is retracted from a surface of the base plate 305.

Figure 42:
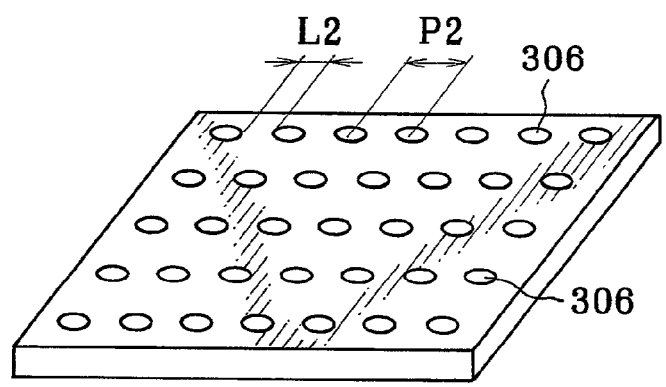
FIG. 42 is a perspective view of a base plate used for the biochemical analysis unit of the fifth embodiment.

In FIG. 42, the base plate 305 has through-holes 306 formed in a predetermined pitch. A distance L2 between the nearest through-holes 306 is usually 0.1–3 mm, and a length or a hole pitch P2 of centers of the nearest through-holes 306 is 0.05–1.5 mm. A width of the base plate 305 is usually 50–1000 μm, preferably 100–500 μm.

A size and the number of the through-hole 306 are as same as those of the through-holes 206. Further, the base plate 305 is formed of the same materials, for example porous materials, as the base plates 5, 125.

Figure 43:
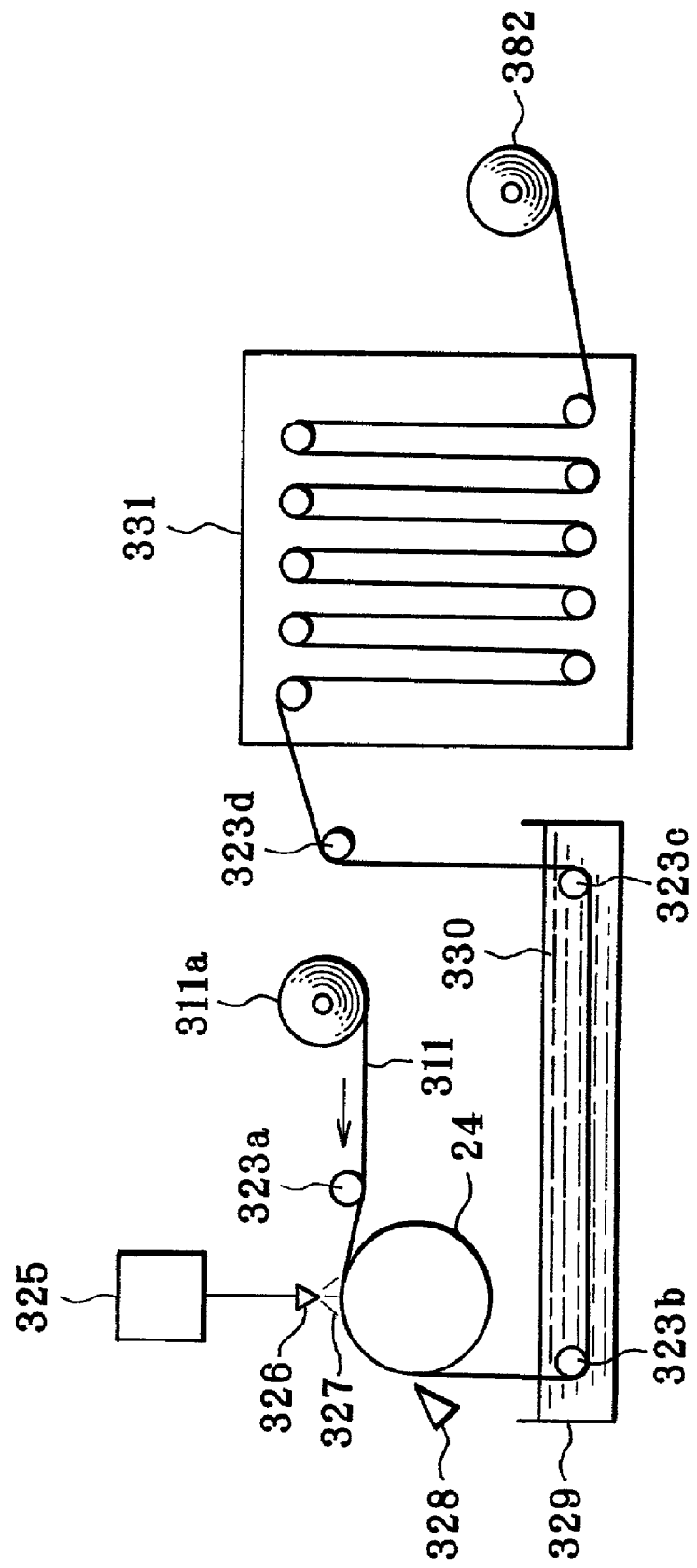
FIG. 43 is a diagrammatic view illustrating a situation of forming absorptive regions in the base plate in FIG. 42.

In FIG. 43, a continuous base plate 311 is fed from a plate roll 311a in an arrowed direction by a roller 323a, and contacts a dram 324. The continuous base plate 311 is moved on the dram 324 to confront to a casting coaster 326. The casting coaster 326 is supplied with a solution 327 of the porous material (or diffusing solution) from a tank 325. The solution 327 is doped (in casting) on the continuous base plate 311 by the casting coaster 326. Thus the solution 327 is provided in the through-holes 306 of the continuous base plate 311. A surface of the dram 324 is previously matted or meshed overall. Accordingly, when the solution 327 is fed out on the continuous base plate 311, an air in the through-holes 306 is expelled out such that the solution 327 may be easily enter in the through-hole 306.

The continuous base plate 311 is further fed in a solidifying vessel 329, and set in an anti-solvent 330 in the solidifying vessel 329 such that the porous material may be shrunken.

The continuous base plate 311 is fed thereafter into a drying room 331 by rollers 323c, 323d. In the drying room 331 the anti-solvent 330 is removed. Thereby, in each through-hole 306 is formed a dried layer composed of materials for porous material. In the dried layer, the extremely small holes are formed.

Then, the continuous base plate 311 is wound by a winding device 332, and thereafter, the continuous base plate 311 is cut into base plates 305 having a predetermined size.

In the present invention, the base plate 305 is not produced only with a producing method described above. For example, after being set in the anti-solvent 330, the continuous base plate 311 may be dried in the air for a predetermined time to form a layer, or washed.

Further, if the porous material is polymer, such as polyamide, the anti-solvent 30 may be removed. In this case, anti-water solution is provided in the through-hole 306, and the polymer is shrunken in the anti-solvent (water). If the porous material is other polymer, such as cellulose, after provided in the through-hole 306, the continuous base plate 311 is dried in the air. Further, if the porous material is ceramics, a diffusing solution is prepared from a material which originally has extremely small holes of predetermined size.

[Embodiment 4]

(1) Produce of a Base Plate Having Through-holes

A polyester sheet has a size 80 mm×80 mm and a width of 120 μm. A density of the polyester sheet is 1.0 g/cm³. Circular holes whose radius is 0.2 mm are formed in the polyester sheet with a hole pitch 0.3 mm, and a distance 0.1 mm. 10×10 holes construct a unit and 6400 holes are formed in the polyester sheet.

| (2) Supply for porous material | |
| --- | --- |
| polysulfone (P-3500, UCC Corporations) | 15 part by weight |
| N-methyl-2-pyrrolidone | 72 part by weight |
| Polyvinyl pyrrolidone | 13 part by weight |
| Water | 1.2 part by weight |

Above materials are solved to prepare a solution for supplying for the porous material. The solution is flown out on the polyester sheet with a casting coaster, supplied in the through-hole. Thereafter, the excess of the solution is removed with a blade. The polyester sheet is set in an air blowing in 1.2 m/s at 25° C., and humidity of 50%. Then, the polyester sheet is set in a water of 25° C. to form the extremely small holes. Thereafter, the polyester sheet is set in diethylene glycol for 5 minuets, washed in water, and dried. Thus the biochemical analysis unit 301 is obtained that is constituted of polyester dissepiments and porous polymer filled area. Herein an average of radius of the holes is 0.2 μm, and a dried layer is formed to be 120 μm in width.

(5) Estimation of Biochemical Analysis Unit

A fragment of nucleic acid is supplied in the absorptive regions 304 of each of the biochemical analysis unit 301. Thereafter, the biochemical analysis unit 301 is set in an aqueous solution of radioactive labeling substances to carry out the hybridization. After withdrawing the biochemical analysis unit from the aqueous solution, it is washed in water and dried. A stimulable phosphor sheet is laid on the biochemical analysis unit and operation of radio autography is carried out in a room temperature. Then, a radioactive data can be read out from the stimulable phosphor sheet in high resolution and high sensitivity.

Figure 44A:
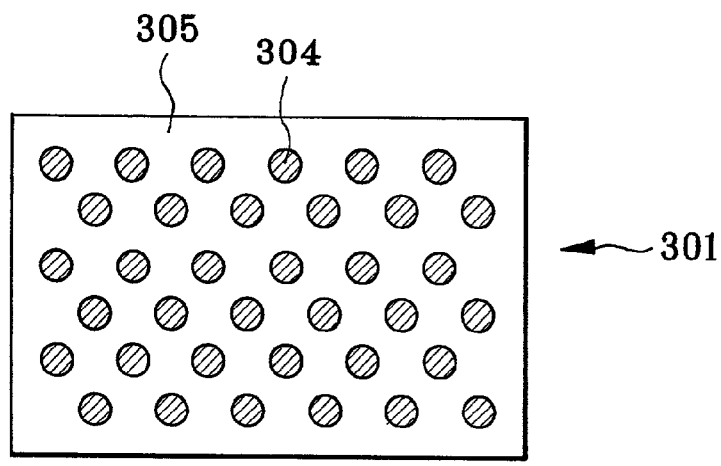
FIG. 44A is a plan view of the biochemical analysis unit of the fifth embodiment, in which the absorptive regions are arranged in another pattern.
Figure 44B:
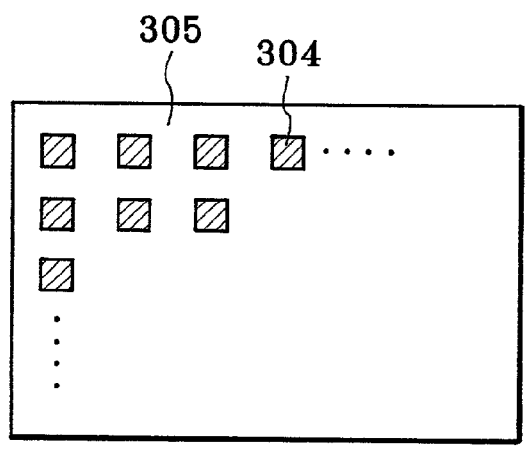
FIG. 44B is a plan view of the biochemical analysis unit of the fifth embodiment, in which the absorptive regions are tetragonaly formed.
Figure 44C:
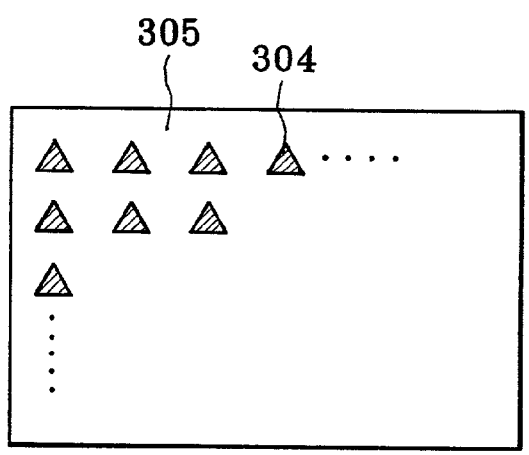
FIG. 44C is a plan view of the biochemical analysis unit of the fifth embodiment, in which the absorptive regions are triangularly formed.

Further, the absorptive regions 304 may be formed in other pattern. As shown in FIG. 44A, each line of the respective absorptive regions 304 is alternatively formed. Furthermore, the absorptive regions 304 may have, for example, triangle-shape in FIG. 44B, and tetragonal-shape in FIG. 44C.

Furthermore, in order to absorb the nucleic acid and the protein more easily, the absorptive region 305 may be processed so as to be hydrophilic.

Figure 45:
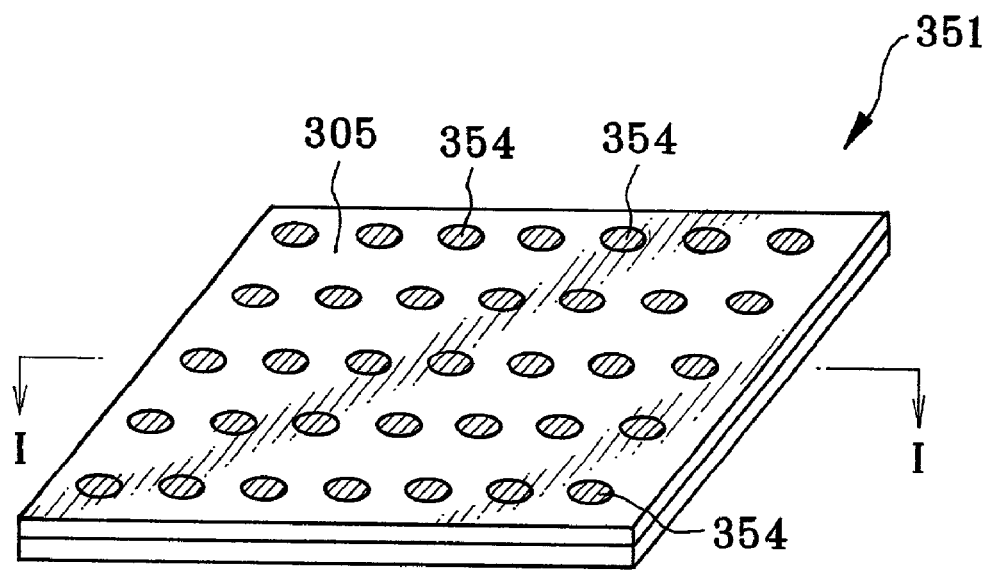
FIG. 45 is a perspective view of a biochemical analysis unit of the sixth embodiment of the present invention.
Figure 46:
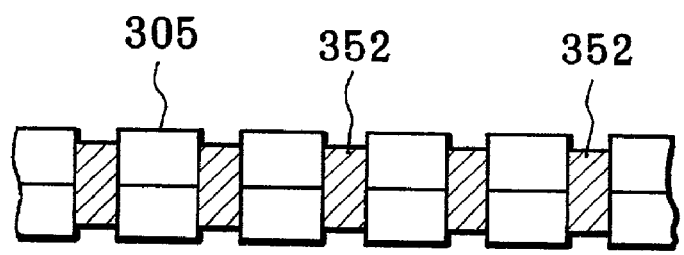
FIG. 46 is a cross-sectional view taken along a line I—I in FIG. 45.

In FIG. 45, a biochemical analysis unit 351 includes the two base plates 305 and absorptive regions 354. As shown in FIG. 46, the absorptive region 354 is retracted from surfaces of the base plates 305.

Figure 47:
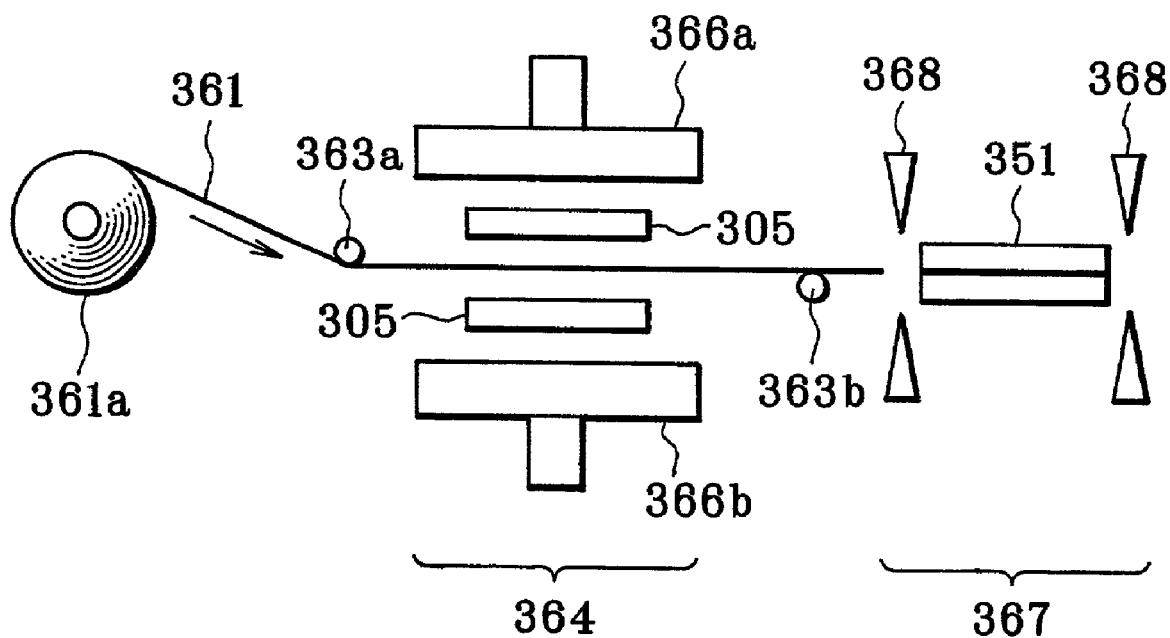
FIG. 47 is a diagrammatic view illustrating a situation of forming the biochemical analysis unit in FIG. 45.

In FIG. 47, an absorptive sheet 361 made of the porous material is fed from a absorptive sheet roll 361a in an arrowed direction to a pressing section 364 by a roller 363a. In the pressing section 364, the two base plates 305 are disposed up- and downward of the absorptive sheet 361 at a predetermined space. When a surface of each base plate 305 is uneven, the base plates 305 are disposed such that the surfaces may confront to each other. The two base plates 305 are pressed by a pressing device 366a to sandwich the absorptive sheet 361, and thereafter fed to a cutting section 367 by a roller 363b. In the cutting section 367, cutters 368 cut off the absorptive sheet roll 361a to form the biochemical analysis unit 351.

Figure 48:
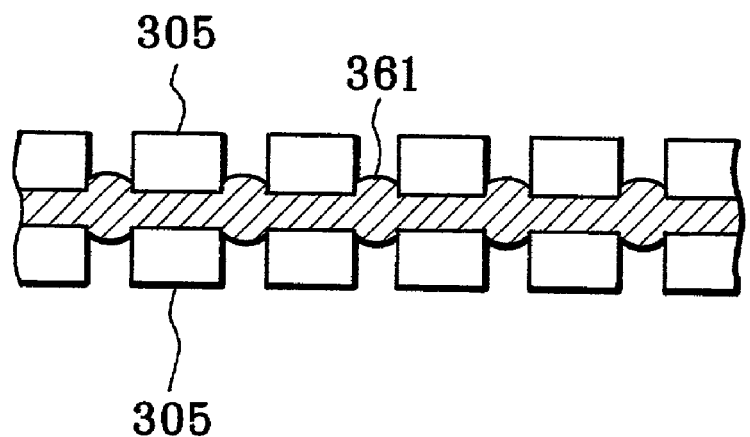
FIG. 48 is a sectional view illustrating a situation of the two base plates and a porous material when the biochemical analysis unit is formed.

The pressing devices 366a are heated and press the two base plates 305 to the absorptive sheet 361 in thermo compression. As shown in FIG. 48, the base plates 305 sandwich the absorptive sheet 361 thereby. The thermal compression is adequate when the base plate 305 is formed of at least one of metals and ceramics. The pressure and the temperature applied for the thermo compression may be changed corresponding sorts and thickness of the base plates 305 and the absorptive sheets 361, and is usually 10–500 $kg/cm^2$, preferably 50–200 $kg/cm^2$.

In order to form the biochemical analysis unit 351, a solvent may be used. As shown in FIG. 49, there are a solvent applying section 374 between the absorptive sheet roll 361a and the pressing section 364, and a drying section 379 between the pressing section 364 and the cutting section 367.

After fed by a roller 373a, the absorptive sheet 361 is set in a solvent in a vessel 375 provided in the solvent applying section 374. Then the absorptive sheet 361 is fed to the pressing section 364 by rollers 373b, 373c, 373d. After thermal compression in the pressing section 364, the pair of the two base plates 305 sandwiching the absorptive sheet 361 is fed in a drying room 380 by a roller 373e. In the drying room 380, an air blow is applied to the pair of the base plates 305 to dry the solvent remaining in the extremely small holes of the absorptive sheet 361. Thereafter, the pair of the base plates 305 is fed in the cutting section 367 to obtain the biochemical analysis unit 351.

As the solvent may be used materials which can solve the base plate 305 but not the absorptive sheet 361. Such material must be decided corresponding to sorts of the base plates 305 and the absorptive sheet 361, and there are for example, acetone, methylethylketone, DMSO (dimethyl sulfoxyde), DMF (dimethyl formamide), methylene chloride, N-methyl-2-piloridrine, chloroform, trichloroethane, benzene, toluene, and the like.

Further, in order to absorb the nucleic acid and the protein more easily, the absorptive region 354 may be processed so as to be hydrophilic.

[Embodiment 4]

(1) Produce of Base Plate

Two base plates coated with nickel are prepared for an electro coating method. Each base plate has a size 80 mm×80 mm and a width of 120 µm. A density of the base plate is 8.8 $g/cm^3$. Circular holes whose radius is 0.2 mm are arranged with a hole pitch 0.3 mm and a distance 0.1 mm. 10×10 holes construct a unit and 6400 holes.

| (2) Supply for porous material | |
|---|---|
| Nylon-6 (Polysciences Corporation) | 14 part by weight |
| Formic acid | 66 part by weight |
| Water | 20 part by weight |

Above materials are solved to prepare a solution for forming porous structure. The solution is doped on the polyesther sheet with a casting coaster, supplied in the through-hole. Thereafter, the excess of the solution is removed with a blade. The base plate is set in 40% formic acid aqueous solution to form the extremely small holes. Thereafter, the base plate is washed in water and dried. Thus the biochemical analysis unit is obtained that is constructed of polyester dissepiments and a porous polymer area. Herein an average of radius of the holes is 0.5 µm, and a dried layer is formed to be 160 µm in width.

| (3) Prepare of porous material | |
|---|---|
| Nylon-6 | 15 part by weight |
| Formic acid | 83 part by weight |
| Water | 2 part by weight |

Above materials are mixed in a room temperature for three hours. The mixture is warmed at 50° C. for one hour and cooled to prepare a polymer solution. The polymer solution is applied and dried to form a porous material sheet. Thereafter, the porous material sheet is set in 20%-formic acid solution to form the extremely small holes. The average of the diameter of the small holes is 0.45 µm.

(4) Unitizing Through Pressing

The porous material is sandwiched between the two base plates, and they are pressed under 50 $kg/cm^2$ and in 150° C. Thereafter, the excess of the porous material is cut off to obtain a biochemical analysis unit.

(5) Estimation of Biochemical Analysis Unit

A fragment of nucleic acid is supplied in porous material of each of the biochemical analysis unit. Thereafter, the biochemical analysis unit is set in an aqueous solution of radioactive labeling substances to carry out the hybridization. After withdrawing the biochemical analysis unit from the aqueous solution, it is washed in water and dried. A stimulable phosphor sheet is laid on the biochemical analysis unit and operation of radio autography is carried out in a room temperature. Then, a radioactive data can be read out from the stimulable phosphor sheet in high resolution and high sensitivity.

Figure 50A:
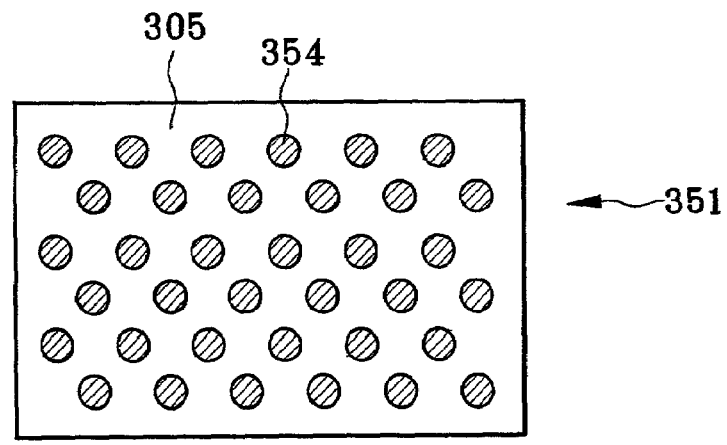
FIG. 50A is a same view of the biochemical analysis unit of the sixth embodiment, in which the absorptive regions are arranged in another pattern.

Further, the absorptive regions 354 may be formed in other pattern. As shown in FIG. 50A, each line of the respective absorptive regions 354 is alternatively formed.

Figure 50B:
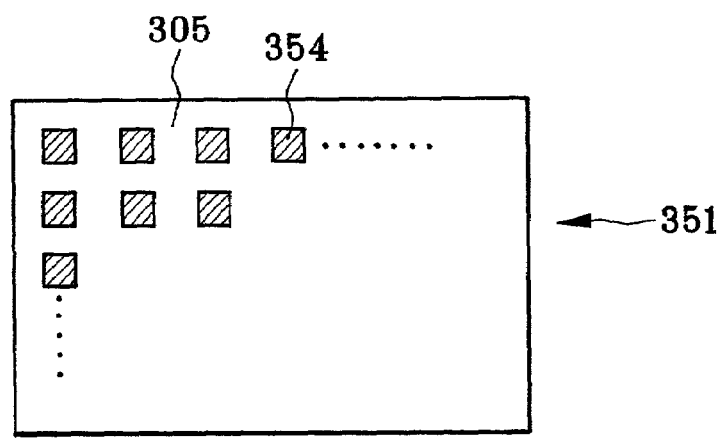
FIG. 50B is a same view of the biochemical analysis unit of the sixth embodiment, in which the absorptive regions are tetragonaly formed.
Figure 50C:
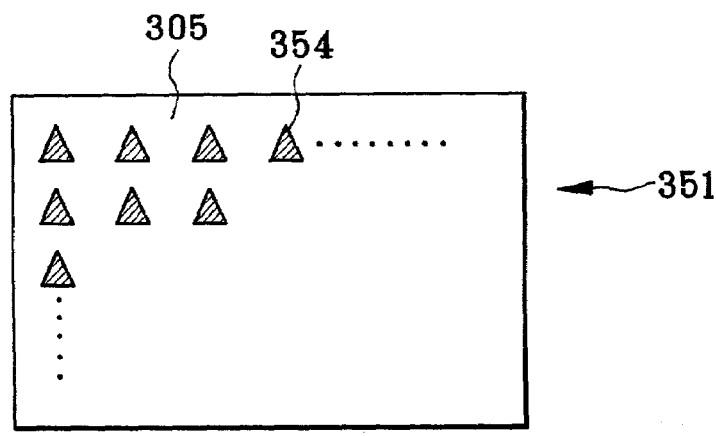
FIG. 50C is a same view of the biochemical analysis unit of the sixth embodiment, in which the absorptive regions are triangularly formed.

Furthermore, the absorptive regions 354 may have, for example, triangle-shape in FIG. 50B, and tetragonal-shape in FIG. 50C.

Various changes and modifications are possible in the present invention and may be understood to be within the present invention.

What is claimed is:

1. A biochemical analysis unit used for analyzing a data of a radioactive ray and a light, comprising:
   a plate member formed of a shielding material which can shield at least one of said radioactive ray and said light, said plate member having a first surface and a second surface;
   plural through-holes formed in said plate member;
   an absorptive membrane formed of an absorptive material, covering said first surface of said plate member, a part of said absorptive membrane provided in said plural through-holes;
   absorptive regions formed of through said through-holes of in said second surface of said plate member;
   wherein the absorptive membrane is provided to fill more than half of the volume of each of the plural through-holes.

2. A biochemical analysis unit as described in claim 1, wherein in said absorptive regions are absorbed specific binding substances which specifically binds with substances derived from living organism that are labeled by at least one of labeling substances including radioactive labeling substances, fluorescent substances and chemiluminescent labeling substances.

3. A biochemical analysis unit as described in claim 2, wherein said specific binding substances and said substances derived from living organism are bound through one of hybridization, antigen-antibody reaction and receptor-ligand.

4. A biochemical analysis unit as described in claim 1, wherein said plate member is fixed to said absorptive membrane through an adhesive agent.

5. A biochemical analysis unit as described in claim 3, wherein said plate member decreases a density of said radioactive ray and the light less than 1/5 when said radioactive ray and the light passes in said plate member at a length corresponding to a distance between the nearest two of said through-holes.

6. A biochemical analysis unit as described in claim 5, wherein said plate member decreases a density of said radioactive ray and the light less than 1/10 when said radioactive ray and the light passes in said plate member at a length corresponding to a distance between the nearest two of said through-holes.

7. A biochemical analysis unit as described in claim 6 wherein said plate member is formed of at least one of metallic materials, ceramic materials and plastic materials.

8. A biochemical analysis unit as described in claim 7, wherein said plate member is formed of said plastic materials containing particles of oxides of metals.

9. A biochemical analysis unit as described in claims 8, wherein said absorptive regions and said plate member form a flat surface.

10. A biochemical analysis unit as described in claim 8, wherein said absorptive regions are retracted from a face of said plate member.

11. A biochemical analysis unit as described in claim 3, wherein the number of said absorptive regions is more than 10.

12. A biochemical analysis unit as described in claim 11, wherein the number of said absorptive regions is more than 1000.

13. A biochemical analysis unit as described in claim 12, wherein the number of said absorptive regions is more than 10000.

14. A biochemical analysis unit as described in claim 3, wherein each of said absorptive regions has a size less than 5 $mm^2$.

15. A biochemical analysis unit as described in claim 14, wherein each of said absorptive regions has a size less than 1 $mm^2$.

16. A biochemical analysis unit as described in claim 15, wherein each of said absorptive regions has a size less than 0.1 $mm^2$.

17. A biochemical analysis unit as described in claim 3, wherein the averaged density of the number of said absorptive regions is more than 10/$cm^2$.

18. A biochemical analysis unit as described in claim 17, wherein the averaged density of the number of said absorptive regions is more than 1000/$cm^2$.

19. A biochemical analysis unit as described in claim 18, wherein the averaged density of the number of said absorptive regions is more than 10000/$cm^2$.

20. A biochemical analysis unit as described in claim 3, wherein said plural absorptive regions are arranged in a pattern.

21. A biochemical analysis unit as described in claim 3, wherein said absorptive material is a porous material.

22. A biochemical analysis unit as described in claim 21, wherein said porous material is a carbon porous material or may be used for membrane filter.

23. A biochemical analysis unit as described in claim 3, wherein said absorptive material contains a fiber material.

* * * * *